(12) United States Patent
Tang et al.

(10) Patent No.: US 12,412,321 B2
(45) Date of Patent: Sep. 9, 2025

(54) METHOD AND SYSTEM TO COMPENSATE FOR CONSECUTIVE MISSING VIEWS IN COMPUTED TOMOGRAPHY (CT) RECONSTRUCTION

(71) Applicant: CANON MEDICAL SYSTEMS CORPORATION, Tochigi (JP)

(72) Inventors: Qiulin Tang, Vernon Hills, IL (US); Thomas Labno, Vernon Hills, IL (US); Jian Zhou, Vernon Hills, IL (US); Liang Cai, Vernon Hills, IL (US); Zhou Yu, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 655 days.

(21) Appl. No.: 17/723,894

(22) Filed: Apr. 19, 2022

(65) Prior Publication Data

US 2023/0215058 A1    Jul. 6, 2023

Related U.S. Application Data

(60) Provisional application No. 63/295,035, filed on Dec. 30, 2021.

(51) Int. Cl.
*G06T 11/00* (2006.01)
*A61B 6/00* (2024.01)
(Continued)

(52) U.S. Cl.
CPC ............ *G06T 11/005* (2013.01); *A61B 6/032* (2013.01); *A61B 6/5205* (2013.01); *G16H 30/20* (2018.01); *G06T 2210/41* (2013.01)

(58) Field of Classification Search
CPC .... G06T 11/005; G06T 11/006; G06T 11/008; G06T 2210/41; A61B 6/032; A61B 6/5205; A61B 6/5258; G16H 30/20; G16H 30/40
See application file for complete search history.

(56) References Cited

U.S. PATENT DOCUMENTS

2004/0165695 A1    8/2004   Karimi et al.
2006/0104407 A1 *  5/2006   Zamyatin ............... G06T 11/005
                                                              378/4
(Continued)

FOREIGN PATENT DOCUMENTS

CN        1781454 A     6/2006
CN      105093342 A    11/2015
(Continued)

OTHER PUBLICATIONS

Zamyatin et al.; "Helical cone beam CT with an asymmetrical detector", Bio-Imaging Research, Inc. | Toshiba America Medical Systems; Sep. 21, 2005.
(Continued)

*Primary Examiner* — John B Strege
(74) *Attorney, Agent, or Firm* — Oblon, McClelland, Maier & Neustadt, L.L.P.

(57) ABSTRACT

A method, system, and computer readable medium to compensate for consecutive missing views in Computed Tomography (CT) reconstruction. By utilizing at least one complementary ray from a previous or subsequent view, the missing view(s) can be filled in. When plural complementary rays exist, a linear or non-linear combination of rays can be used to fill in the missing views, and the weights used in the combination may be smoothed to prevent over-emphasis of the replacement views.

20 Claims, 26 Drawing Sheets

(51) Int. Cl.
*A61B 6/03* (2006.01)
*G16H 30/20* (2018.01)

(56) References Cited

U.S. PATENT DOCUMENTS

| | | | | |
|---|---|---|---|---|
| 2006/0159327 | A1* | 7/2006 | Kohler | A61B 6/027 |
| | | | | 382/131 |
| 2007/0081622 | A1* | 4/2007 | Bruder | A61B 6/032 |
| | | | | 378/7 |
| 2011/0293155 | A1* | 12/2011 | Nakanishi | G06T 11/005 |
| | | | | 382/131 |
| 2012/0093281 | A1* | 4/2012 | Zamyatin | A61B 6/4085 |
| | | | | 378/15 |
| 2020/0118308 | A1* | 4/2020 | Nakanishi | A61B 6/032 |
| 2020/0170585 | A1* | 6/2020 | Yu | A61B 6/5258 |
| 2020/0196973 | A1 | 6/2020 | Zhou et al. | |

FOREIGN PATENT DOCUMENTS

| | | |
|---|---|---|
| CN | 107714072 A | 2/2018 |
| JP | 2003-116841 A | 4/2003 |
| JP | 2003-135448 A | 5/2003 |

OTHER PUBLICATIONS

Office Action issued Jul. 15, 2025, in corresponding Chinese Patent Application No. 202211708860.1, citing documents 15-17 therein, 9 pages.

* cited by examiner

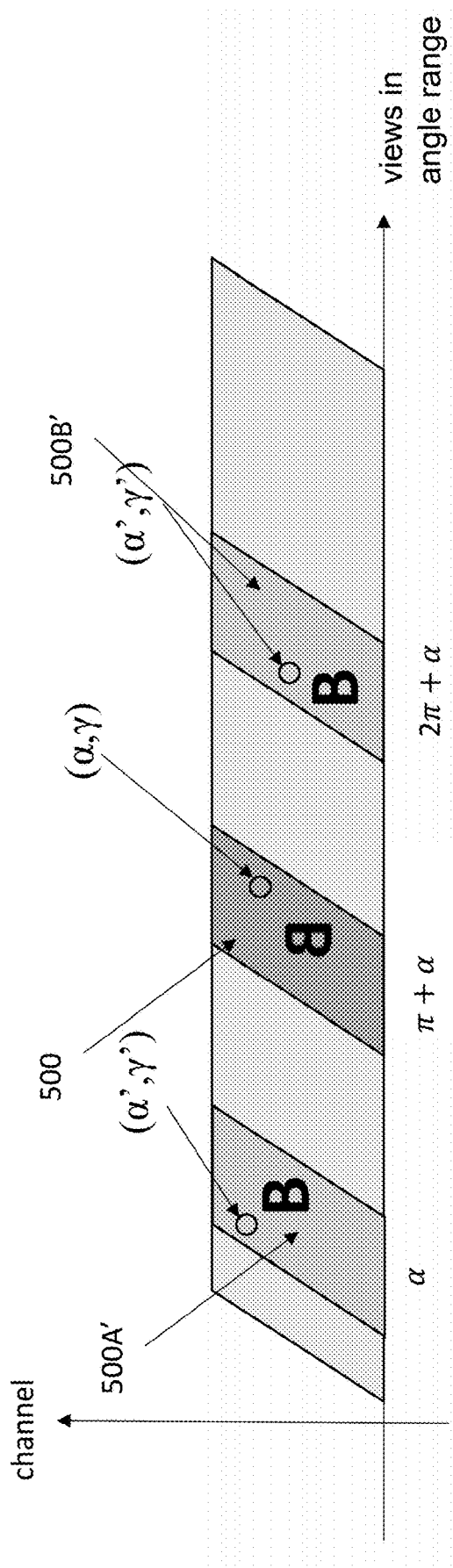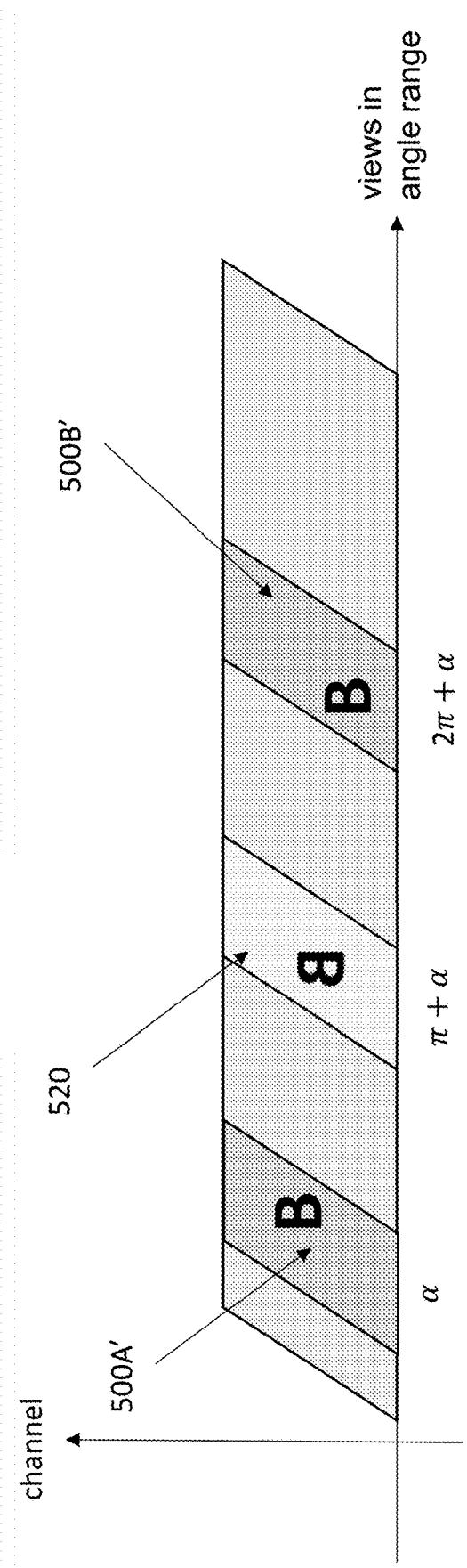
FIG. 5C
FIG. 5D

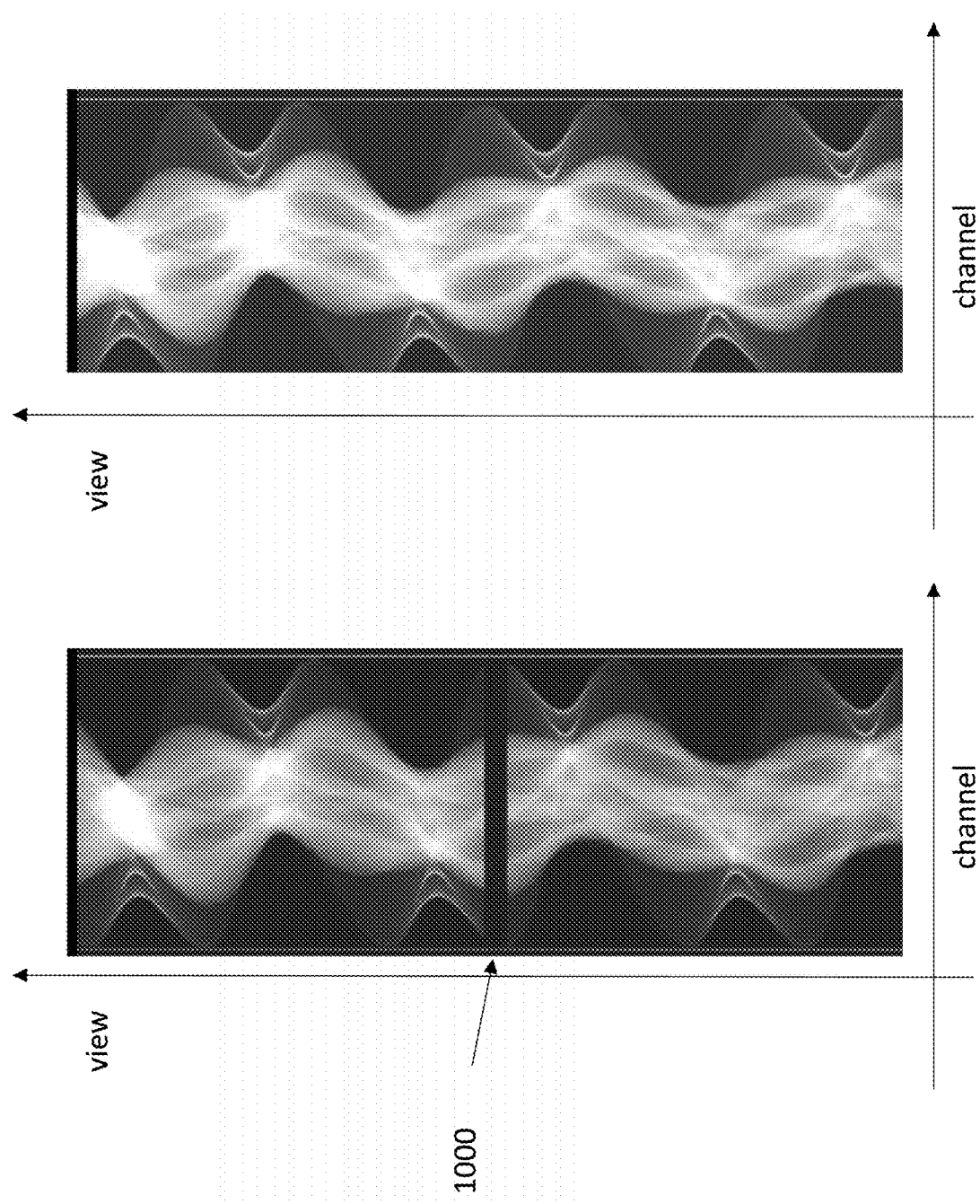

METHOD AND SYSTEM TO COMPENSATE FOR CONSECUTIVE MISSING VIEWS IN COMPUTED TOMOGRAPHY (CT) RECONSTRUCTION

CROSS-REFERENCE TO CO-PENDING APPLICATION

The present application relates to and claims priority under 35 U.S.C. § 119(e) to U.S. Provisional Patent Application No. 63/295,035 filed on Dec. 30, 2021, the contents of which are incorporated herein by reference.

FIELD OF THE INVENTION

The present invention is directed to a method and system for compensating for consecutive missing views in Computed Tomography (CT) reconstruction, and in one embodiment to utilizing complementary rays to fill-in the missing views.

BACKGROUND

In X-ray Computed Tomography (CT), a CT image is constructed from a number of views taken of a subject during which time X-rays are directed through a subject and toward an x-ray detector. The views are taken at different angles as the X-ray emitter and the X-ray detector are moved around the subject in a generally circular motion. In addition, the subject is generally lying down, and the table on which the subject is lying is moved to enable a larger portion of the subject to be scanned. The resulting movement of the subject and the movement of the X-ray transmitter/detector creates a helical scanning of the subject.

During CT scanning, the CT scanner may determine that the data associated with the detectors for the corresponding view should be considered unreliable. The CT scanner thus treats the data for the view during the unreliable time period as "missing."

Interpolation is often applied to fill the missing views during image reconstruction. For example, as shown in FIG. 20A, a number of consecutive missing views 1000 (depicted as a black bar in the middle of the views) should have been obtained for a number of channels of a CT scanner. To compensate for the missing views, interpolation can be performed using data from the correctly obtained adjacent views to "fill-in" the missing views, as shown in FIG. 20B. However, if the number of missing views is large, interpolation, especially linear interpolation, is often insufficient to generate reconstructed image without artifacts.

FIG. 21A illustrates an original reconstructed image generated using all of the views obtained during a scan of soft tissue where no views were considered "missing." FIG. 21B illustrates a test reconstructed image generated using the data of FIG. 21A but by removing a number of consecutive views to simulate "missing" views before the reconstructed image was generated. As can be seen in the circled portions of FIG. 21B, the resulting image experiences degradation (e.g., streaking) as compared to original FIG. 21A. FIG. 21C illustrates a test reconstructed image generated using the data of FIG. 21A but by removing a number of consecutive views to simulate "missing" views. Before the reconstructed image of FIG. 21C was generated, linear interpolation was performed on the views to fill-in the missing view data. As can be seen in the circled portions of FIG. 21C, the resulting image experiences degradation (e.g., streaking) as compared to original FIG. 21A.

FIG. 22A illustrates an original reconstructed image generated using all of the views obtained during a scan of a portion of human lungs where no views were considered "missing." FIG. 22B illustrates a test reconstructed image generated using the data of FIG. 22A but by removing a number of consecutive views to simulate "missing" views before the reconstructed image was generated. As can be seen in the circled portion of FIG. 22B, the resulting image experiences degradation (including shading) as compared to original FIG. 22A. FIG. 22C illustrates a test reconstructed image generated using the data of FIG. 22A but by removing a number of consecutive views to simulate "missing" views. Before the reconstructed image of FIG. 22C was generated, linear interpolation was performed on the views to fill-in the missing view data. As can be seen in FIG. 22C, the resulting image experiences degradation (e.g., streaking) as compared to original FIG. 22A.

SUMMARY

As described herein, a method, system, and computer readable medium compensate for consecutive missing views in Computed Tomography (CT) reconstruction. By utilizing at least one complementary ray from a previous or subsequent view, the missing view(s) can be filled in. When plural complementary rays exist, a linear or non-linear combination of rays can be used to fill in the missing views, and the weights used in the combination may be smoothed to prevent over-emphasis of the replacement views.

BRIEF DESCRIPTION OF THE DRAWINGS

FIG. 5C illustrates that a missing view can be corrected using a preceding view or a combination of a preceding view and a subsequent view, both of which have at least one complementary ray to a number of the rays missing from the missing view.

FIG. 5D illustrates a replacement view having been calculated by a weighted combination of at least two complementary views.

FIGS. 11A-11D are exemplary numerical weightings of a subset of the views to which modified weights are applied due to missing views.

FIG. 20A is an image showing a number of consecutive missing views (depicted as a black bar in the middle of the views) taken for a number of channels by a CT scanner.

FIG. 20B is an image of the views of FIG. 20A and a set of estimated views produced by interpolation.

DETAILED DESCRIPTION

Figure 1:
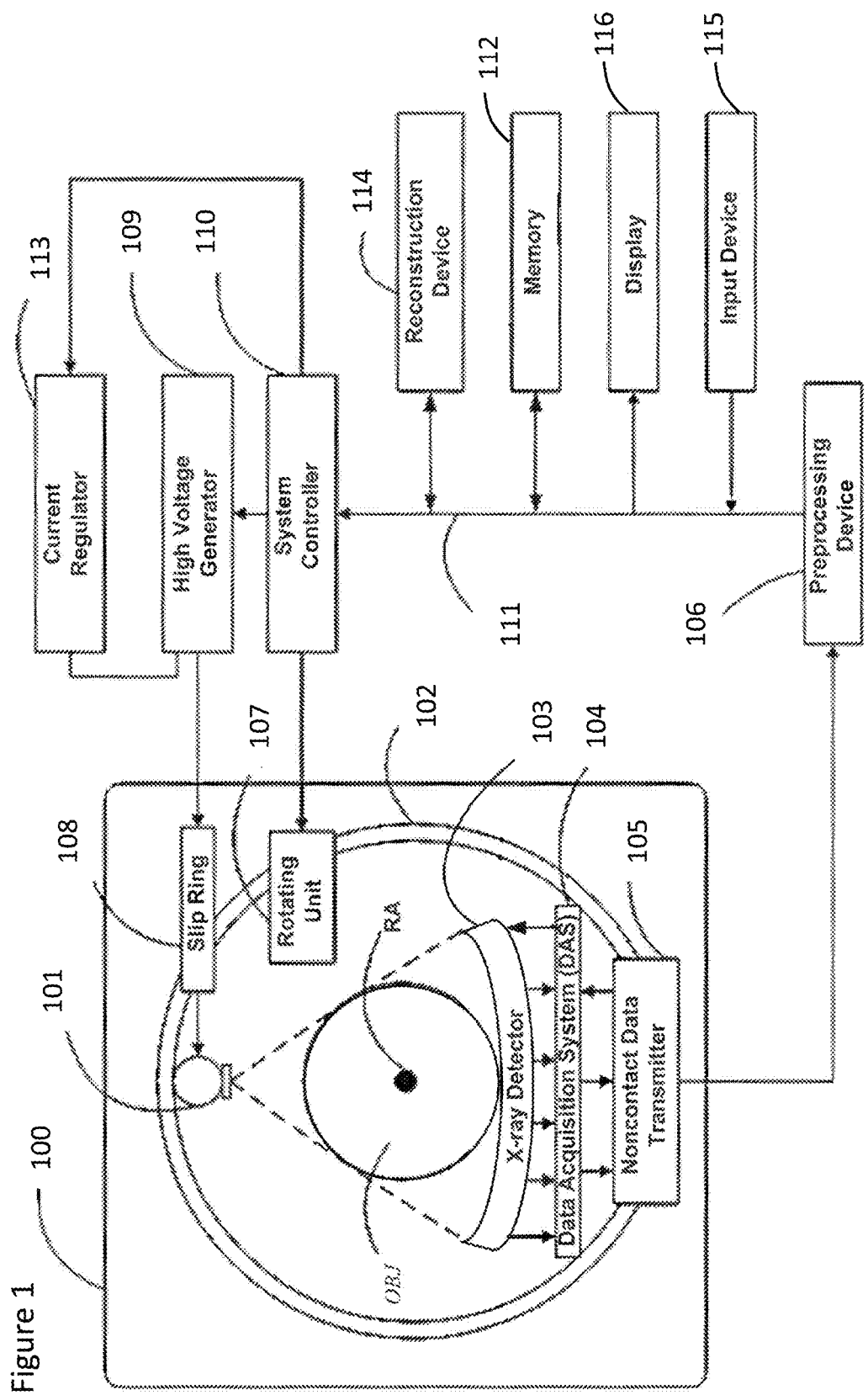
FIG. 1 shows a schematic drawing of one implementation of a CT apparatus having a source and detectors for measuring CT projection data.

Referring now to the drawings, wherein like reference numerals designate identical or corresponding parts throughout the several views. FIG. 1 illustrates an implementation of a radiography gantry included in a CT apparatus or scanner. As shown in FIG. 1, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating apparatus 107 rotates the annular frame 102 at a high speed, such as 0.4 sec/rotation, while the object OBJ is being moved longitudinally along the axis RA into or out of the illustrated page.

Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high-voltage generator 109 that generates a tube voltage applied to the X-ray tube 101 through a slip ring 108 so that the X-ray tube 101 generates X-rays. The X-rays are emitted towards the object OBJ, whose cross sectional area is represented by a circle. The X-ray detector 103 is located at an opposite side from the X-ray tube 101 across the object OBJ for detecting the emitted X-rays that have been transmitted through the object OBJ. The X-ray detector 103 further includes individual detector elements or modules.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 800 TPPR, 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data, at a stage immediately before reconstruction processing. The memory 112 is connected to a system controller 110 through a data/control bus 111, together with a reconstruction device 114, input device 115, and display 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The memory 112 can store the measurement value representative of the irradiance of the X-rays at the X-ray detector unit 103. Further, the memory 112 can store a dedicated program that executes. e.g., the CT image reconstruction method 300 discussed herein.

The reconstruction device 114 can execute the CT image reconstruction method 300 discussed herein. Further, reconstruction device 114 can execute pre-reconstruction processing image processing such as volume rendering processing and image difference processing as needed. The pre-reconstruction processing of the projection data performed by the preprocessing device 106 can include correcting for detector calibrations, detector nonlinearities, polar effects, noise balancing, and material decomposition. Post-reconstruction processing performed by the reconstruction device 114 can include filtering and smoothing the image, volume rendering processing, and image difference processing as needed. The image reconstruction process can be performed using filtered back-projection (FBP), iterative image reconstruction methods, or stochastic image reconstruction methods. The reconstruction device 114 can use the memory 112 to store, e.g., projection data, reconstructed images, calibration data and parameters, and computer programs.

The reconstruction device 114 can include processing circuitry (e.g., a CPU that can be implemented as discrete logic gates, as an Application Specific Integrated Circuit (ASIC), a Field Programmable Gate Array (FPGA) or other Complex Programmable Logic Device (CPLD)). An FPGA or CPLD implementation may be coded in VHDL, Verilog, or any other hardware description language and the code may be stored in an electronic memory directly within the FPGA or CPLD, or as a separate electronic memory. Further, the memory 112 can be non-volatile, such as ROM, EPROM, EEPROM or FLASH memory. The memory 112 can also be volatile, such as static or dynamic RAM, and a processor, such as a microcontroller or microprocessor, can be provided to manage the electronic memory as well as the interaction between the FPGA or CPLD and the memory.

Alternatively, the processing circuitry (e.g., a CPU) in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor or i3, i5, i7, or i9 from Intel of America or an Opteron or Ryzen processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 116. The display 116 can be an LCD display, CRT display, plasma display, OLED, LED or any other display known in the art.

The memory 112 can be a hard disk drive, CD-ROM drive, DVD drive, FLASH drive, RAM, ROM or any other electronic storage known in the art.

Figure 2A:
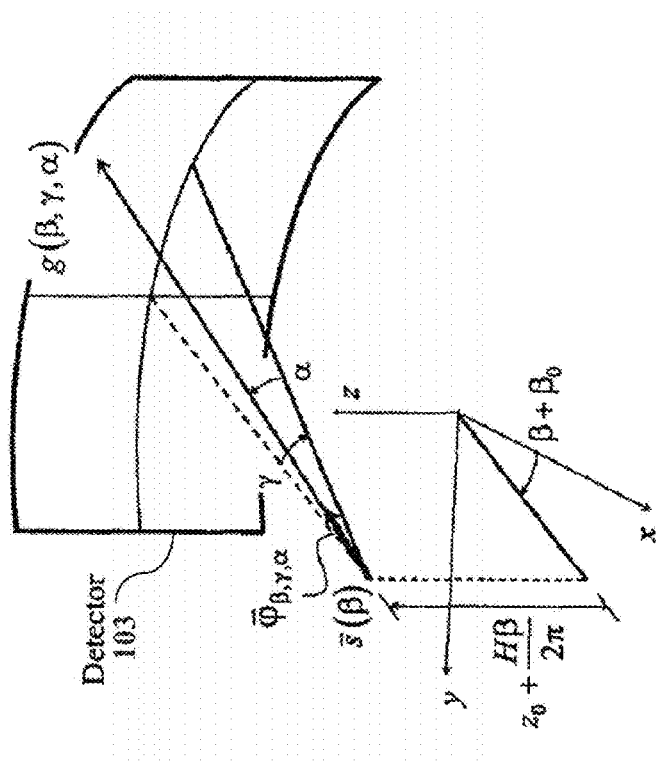
FIG. 2A shows a diagram of a ray from an X-ray beam incident on a detector and nomenclature describing the focus location, the projection angle of the beam, and the angle of a ray within the beam.

FIG. 2A shows a cone-beam geometry of a ray from the X-ray tube 101 to the X-ray detector 103. In general, the projective measurements of the rays can be expressed as the line integral $$g(\beta,\gamma,\alpha)=\int_0^\infty f(s(\beta)+l\varphi_{\beta,\gamma,\alpha})dl,$$

$$s(\beta)=[R\cos(\beta+\beta_0), R\sin(\beta+\beta_0), z_0+H\beta/2\pi]^T,$$

where f(r) is the object to reconstruct, R is the radius of the helical orbit, H is the helical pitch (table feed per rotation), $(\beta,\gamma,\alpha)$ denote projection, ray, and cone angle, respectively (see FIG. 1), and $\varphi_{\beta,\gamma,\alpha}$ denotes the unit vector directed from the X-ray focus s($\beta$) toward the point ($\gamma,\alpha$) on the cylindrical detector surface at $\beta$, where $$\varphi_{\beta,\gamma,\alpha}=[-\cos(\beta+\beta_0+\gamma)\cos\alpha, -\sin(\beta+\beta_0+\gamma)\cos\alpha, \sin\alpha]^T.$$

At $\beta=0$, the focus is in the plane of interest $z=z_0$ at projection $\beta_0$.

Figure 2B:
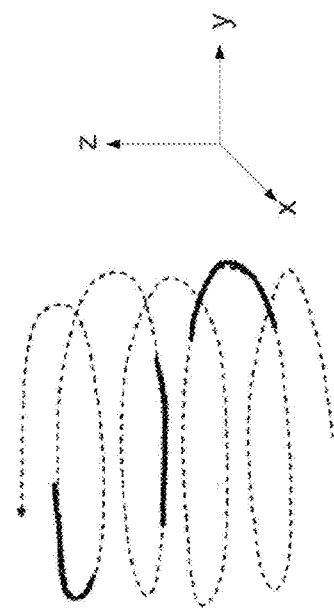
FIG. 2B shows an example of a helical path of an X-ray source around an imaged object.

FIG. 2B shows an example of a helical path of the X-ray tube about the imaged object OBJ. In certain implementations, the object OBJ will be placed on a table that is translated linearly as the X-ray tube 101 and X-ray detector 103 are rotated along respective circular paths, such that the path of the X-ray-tube 101 traverses a helical path relative to the object OBJ. In certain implementations, the projection angle $\beta$ is related to the variables time t and position z by the expressions"

$$t/T_{rot}=\beta/2\pi=(z+z_0)/H$$

so that t=$\beta$=0 when the source is at the slice of interest $z_0$.

In one implementation, projection data is acquired without translating the imaged object OBJ relative to the X-ray tube 101 and X-ray detector 103. This scenario of circular (as opposed to helical) trajectories results in simplifying the analysis by setting H=0. The nomenclature for the ray shown in FIG. 2A is generally applicable to all X-ray beams including cone beams and fan beams. In a fan beam geometry (e.g., a parallel fan beam wherein the X-rays are divergent in one dimension and collimated in another dimension), the analysis can be simplified by setting $\alpha$=0.

Figure 3:
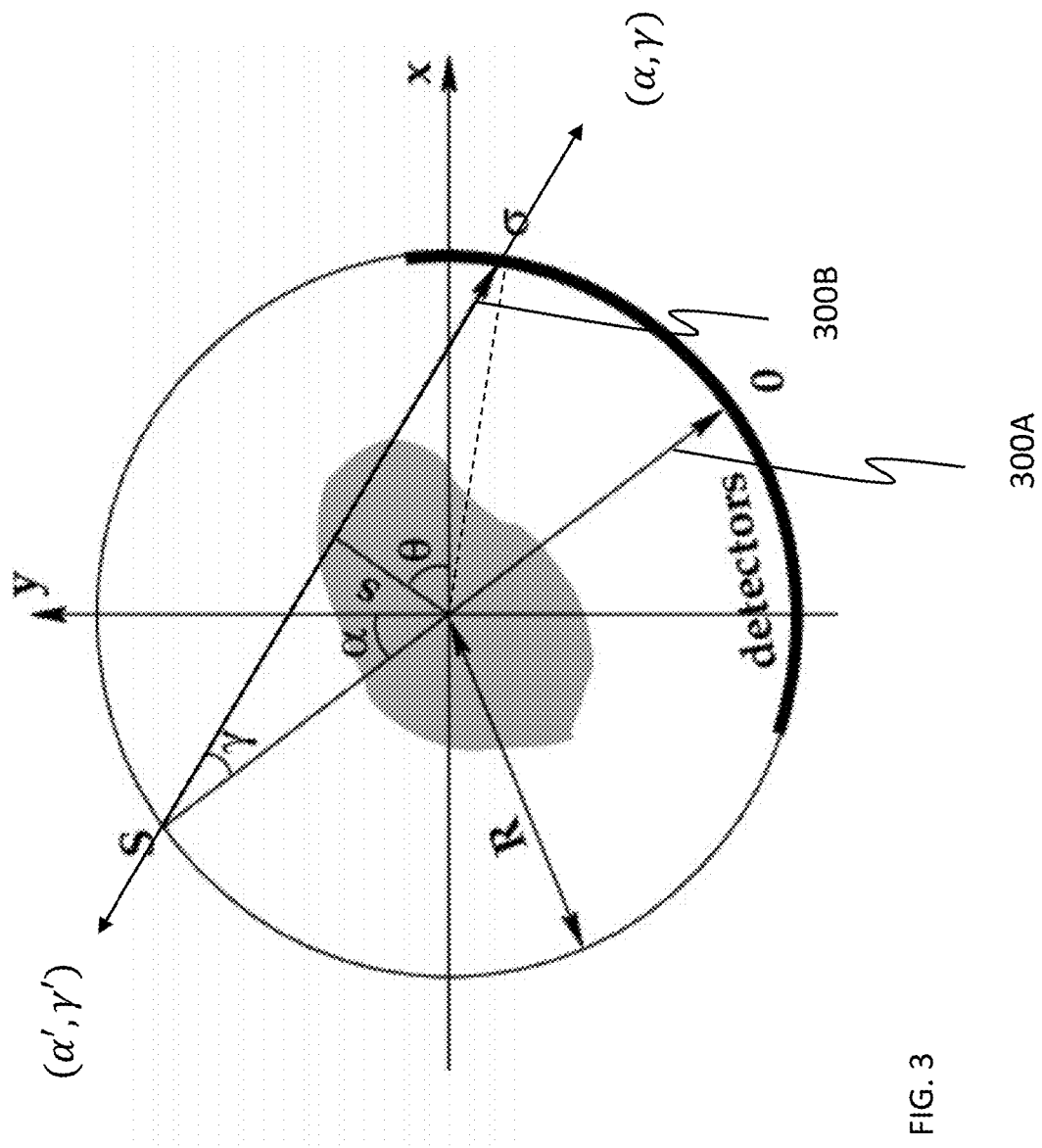
FIG. 3 shows first and second rays impinging upon and being detected by a set of curved detectors having been transmitted from an x-ray source S and indicating a direction of a complementary ray ($\alpha',\gamma'$) to the second ray.

FIG. 3 shows first and second rays 300A/B impinging upon and being detected by a set of curved detectors having been transmitted from an x-ray source S. The first ray 300A is shown arriving at a center of the detectors at position 0, and the second ray 300B is shown as arriving at position σ. If those rays were part of a view that was unusable or missing, then the data that would have been collected about how the x-rays were absorbed by the object at the illustrated angle would be lost.

In the presence of unusable or missing views, it is possible to instead of performing interpolation to perform data replacement using at least one complementary ray from a previous or subsequent view As shown in FIG. 3, the second ray 300B is defined by an angle pair (α,γ), where α represents the tube angle (or view angle) and γ represents the fan angle (relative to the y axis) and corresponding to the channel of the detectors that was intended to detect the ray. In a view in which the second ray (α,γ) 300B is not detected because it corresponds to a missing view, the missing view data (also referred to as "data on a missing view" or "data on missing views") can instead be replaced by a complementary ray (having a direction (α',γ')) that passes along the same path as the second ray 300B but in the complementary direction.

Figure 4B:
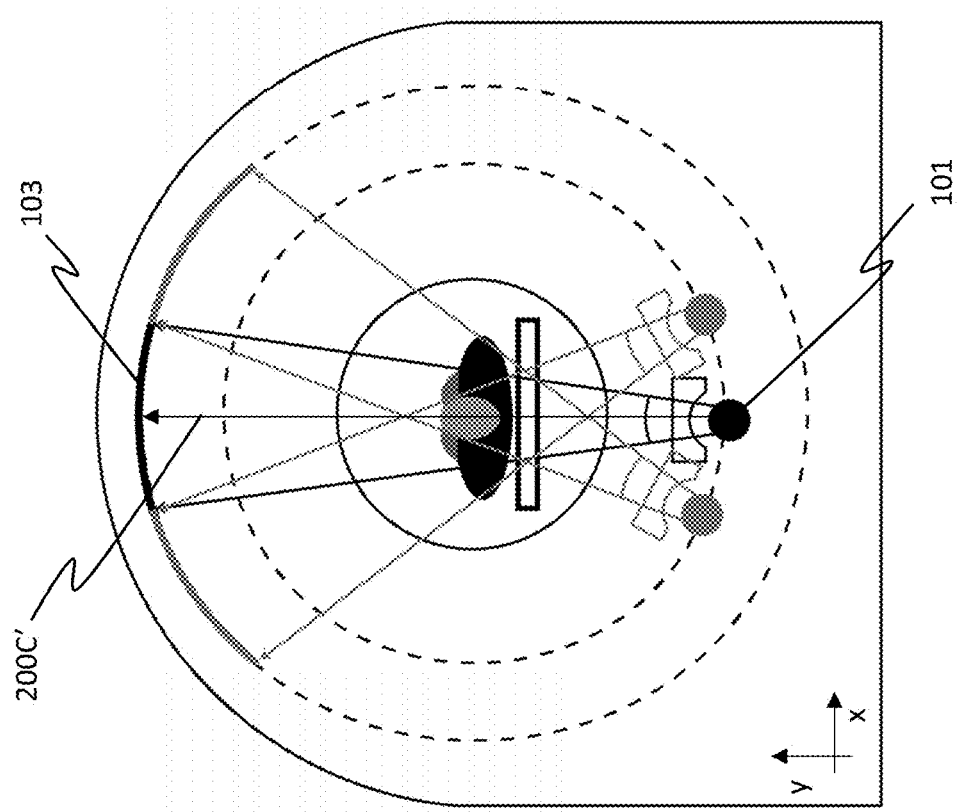
FIG. 4B illustrates an X-ray tube and an X-ray detector oriented vertically so as to have a view angle $\alpha=\pi$ radians (or 180 degrees from the original orientation of FIG. 4A).
Figure 4A:
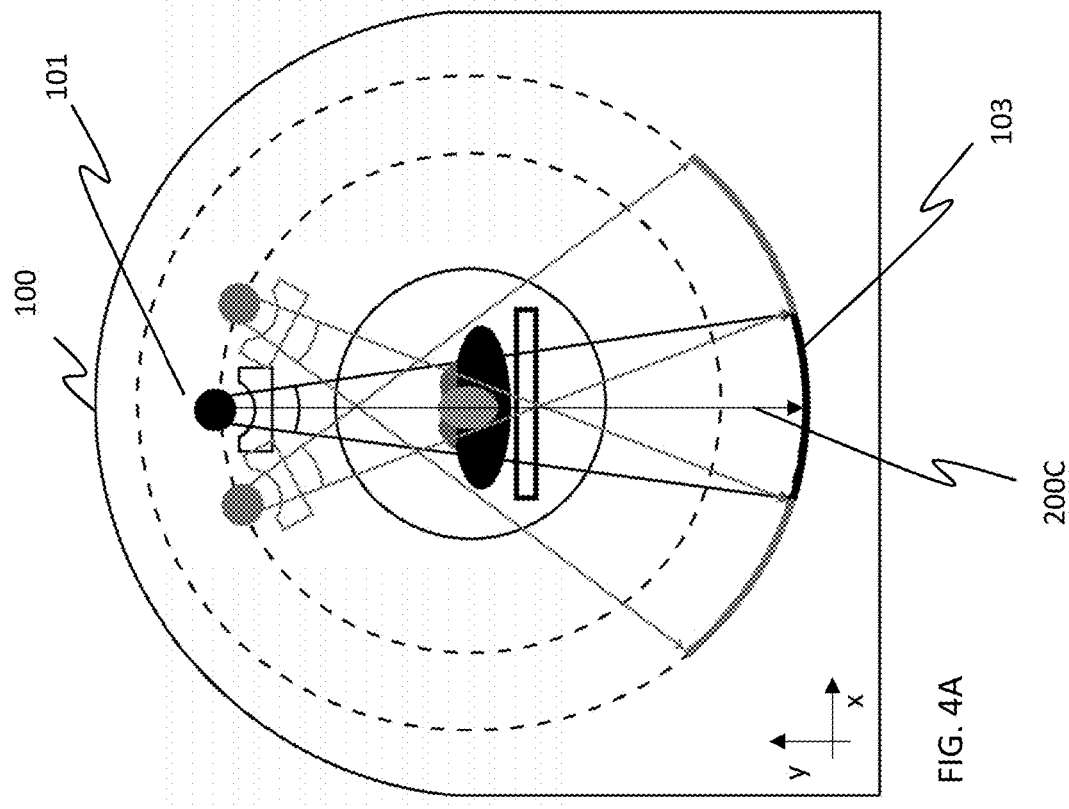
FIG. 4A illustrates an X-ray tube and an X-ray detector oriented vertically so as to have a view angle $\alpha=0$ radians.

As shown in FIGS. 4A and 4B, the X-ray tube 101 and X-ray detector 103 are moved through a series of views. In FIG. 4A, the vertically oriented X-ray tube 101 and X-ray detector 103 shown as having dark shading are oriented so as to have a view angle α=0 radians (using the y-axis as a reference point as in FIG. 3). FIG. 4A is illustrated as also having light grey colored versions of the X-ray tube 101 and X-ray detector 103. Those versions depict the orientation of the X-ray tube 101 and X-ray detector 103 when a preceding and a subsequent view are acquired. By comparison, FIG. 4B shows the X-ray tube 101 and X-ray detector 103 on the opposite side of the patient being imaged as compared to FIG. 4A. The orientation of the tube/detector configurations in FIG. 4B are at α=π radians (or 180 degrees from the original orientation).

FIG. 4A also illustrates a ray 200C that is emitted at a fan angle γ=0 radians and passes through the subject and contacts the center of the detectors 103. FIG. 4B illustrates a complementary ray 200C' that is emitted also at a fan angle γ'=0 and passes through the subject and contacts the center of the detectors 300. In general, a ray having an angle pair (α,γ), and its complementary ray having an angle pair (α',γ') satisfy two equations:

$$\gamma'=-\gamma, \text{ and } \alpha'=\pi+\alpha+2\gamma.$$

Using the examples of FIGS. 4A and 4B above, it can be seen that:

$$\gamma'=0=-\gamma, \text{ and } \alpha'=\pi+(\alpha=0)+2(\gamma=0)=\pi$$

Thus, using those equations, it is possible to process rays from at least one other subsequent or preceding view to obtain data that would otherwise be missing from the data used to generate a reconstructed image.

Figures 5A, 5B:
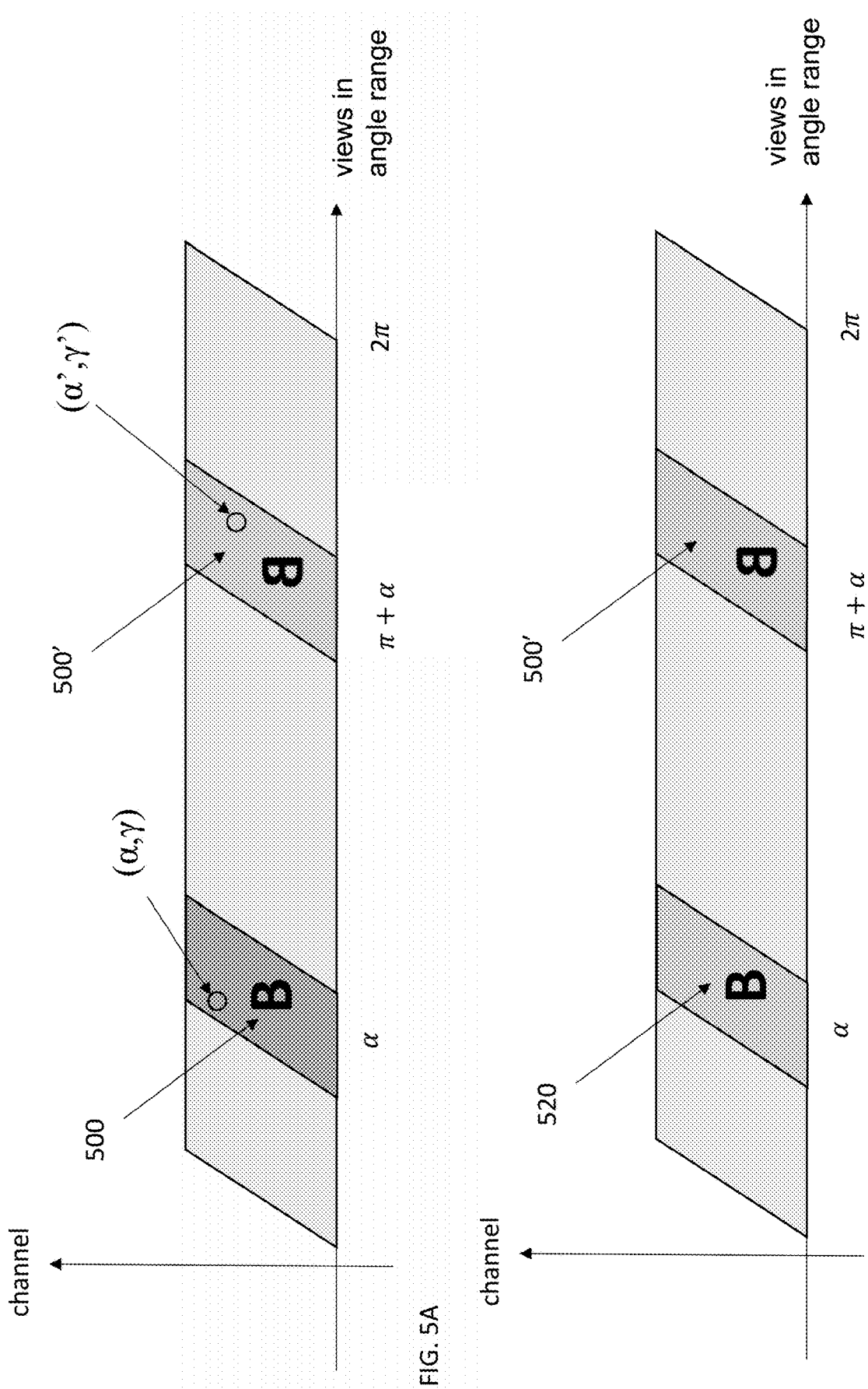
FIG. 5A illustrates a series of views including at least one missing view 500 for which at least one ray having an angle pair ($\alpha,\gamma$) should have been captured as part of the process of capturing a portion of the subject being imaged.
FIG. 5B illustrates a resulting set of images where the missing view 500 has been replaced by view 520 which includes information from at least a preceding complementary view 500'.

As shown in FIG. 5A, a series of views includes at least one missing view 500 for which at least one ray having an angle pair (α,γ) should have been captured as part of the process of capturing a portion of the subject being imaged. For illustrative purposes, the portion that should have been captured is shown as the letter "B" to be able to emphasize the reversing nature of the image being captured. By utilizing at least one ray having an angle pair (α',γ') from at least one complementary view 500' (illustrated as a subsequent view that captured the "B" in reverse), the system is able to fill in missing data for the at least one missing view 500. FIG. 5B shows a resulting set of images where missing view 500 has been replaced by a replacement view 520 which includes information from at least the complementary view 500'.

As shown in FIG. 5C, it is also possible that the missing view 500 can be corrected using a preceding view 500A' or a combination of a preceding view 500A' and a subsequent view 500B', both of which have at least one complementary ray to a number of the rays missing from view 500. As shown in FIG. 5D, the replacement view 520 is a different shading than any of the missing view 500, and either of the complementary views 500A' and 500B'. This difference in shading is intended to signify that the replacement view 520 may be calculated by a weighted combination of at least two complementary views 500A' and 500B'.

Figure 5E:
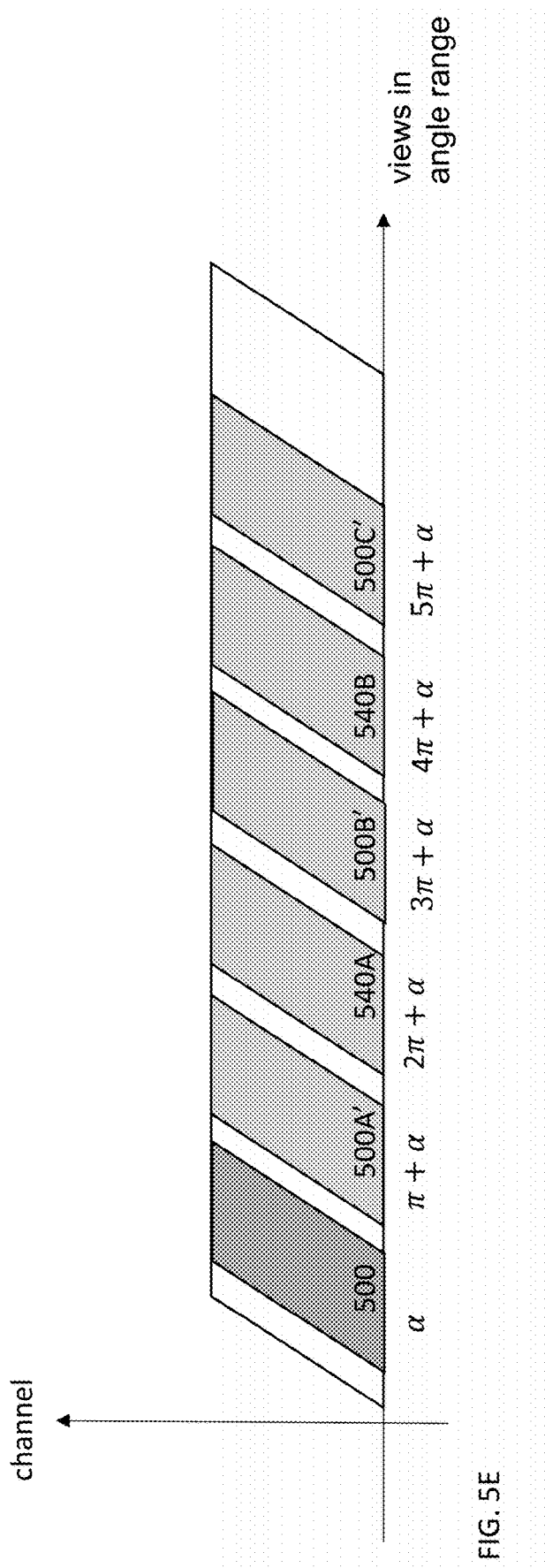
FIG. 5E illustrates that a missing view can be corrected using an asymmetric set of complementary views.
Figure 5F:
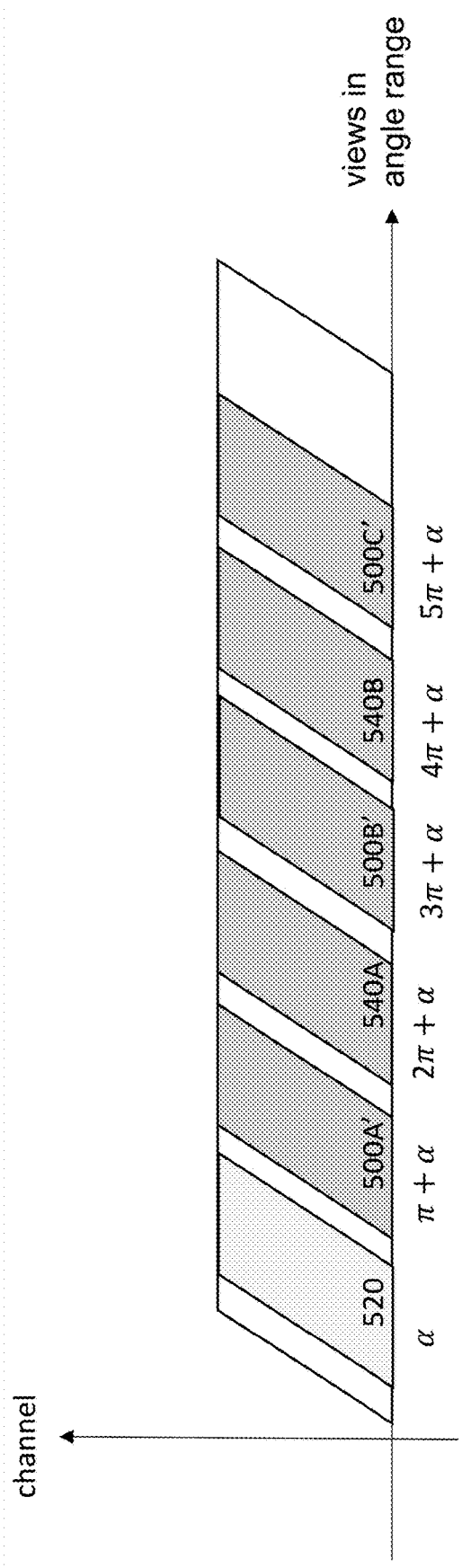
FIG. 5F illustrates a replacement view having been calculated by a weighted combination of at least two complementary views.

As shown in FIG. 5E, the complementary views 500A', 500B', and 500C' used to fill-in for a missing view 500 can be taken from any portion of the existing complementary views and need not be taken symmetrically from existing complementary views. Indeed, in a case where missing views occurred at a beginning of imaging, it would not be possible to use earlier complementary views, but only subsequent complementary views. FIG. 5F illustrates that a replacement view 520 is used instead of the missing view 500, and the replacement view is preferably created as a weighted combination of at least two complementary views 500A' and 500B', and in one embodiment to a weighted combination of at least three complementary views 500A', 500B', and 500C'. In one such embodiment, the weighted combination is formed from all complementary views for which there are rays that can replace data from the missing view 500 with the values of the complementary views but normalized so that all of the rays have the same redundancy (e.g., by each being weighted by 0.5 if there are two complementary rays and by ⅓ if there are 3 complementary rays).

Figure 6B:
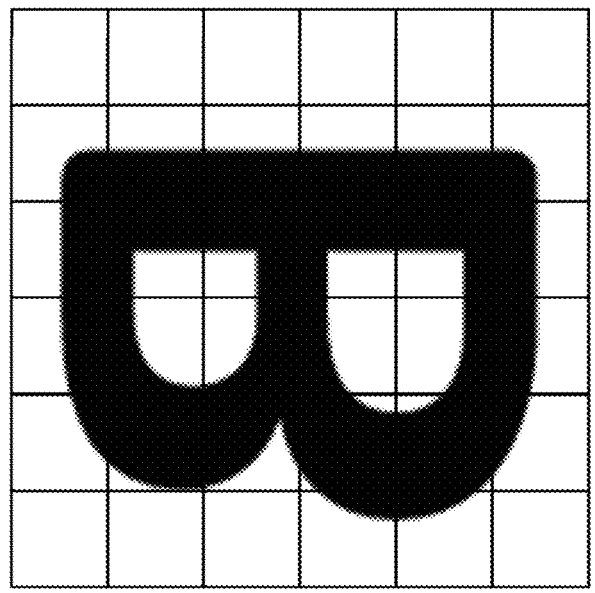
FIG. 6B illustrates an exemplary set of complementary rays captured that correspond to the missing portion of FIG. 6A that are then subject to interpolation to relocate the complementary rays to where the original rays would have been.
Figure 6A:
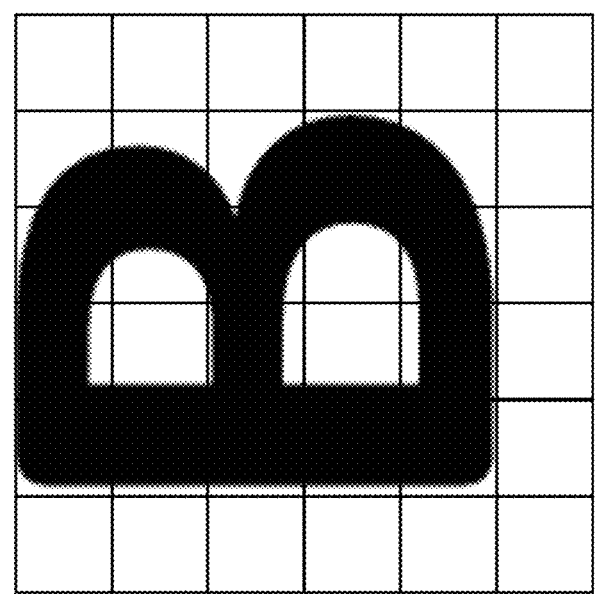
FIG. 6A illustrates how a portion of a missing view would have been captured by detector elements had it properly been captured.

As would be appreciated by those of skill in the art, the complementary rays being used to fill in the data missing from missing view 500 may not all be in the same view and may, because of how much rotation occurs between each view, cross over more than one view. Moreover, in a case where more than one consecutive view is missing, an increasing number of complementary views will be used to provide replacement rays for the missing view 500. Furthermore, because the rotation amounts between views is often unlikely to cause there to be a channel/detector element at exactly the right location to allow a complementary ray having an angle pair (α',γ') to be found to compensate for a missing ray having an angle pair (α,γ), the system and method described herein may further adjust for the shift in the detected rays by interpolating between neighboring channels/detector elements. For example, a missing view that should have acquired rays as shown in FIG. 6A may be able to utilize complementary rays to produce an image such as is shown in FIG. 6B. However, the shift in the rays cause portions of the image of FIG. 6A to be shared across neighboring channels/detector elements. Thus, the method and system utilize a weighted average of neighboring pixels to shift the detected rays in the complementary views back to their corresponding locations in the missing views. It will be assumed for the rest of this discussion that the use of complementary rays is done based on interpolated complementary rays, although in some embodiments it may be possible to use non-interpolated complementary rays (e.g., when a smoothing or other filtering is going to be performed on the rays anyway).

Figure 7:
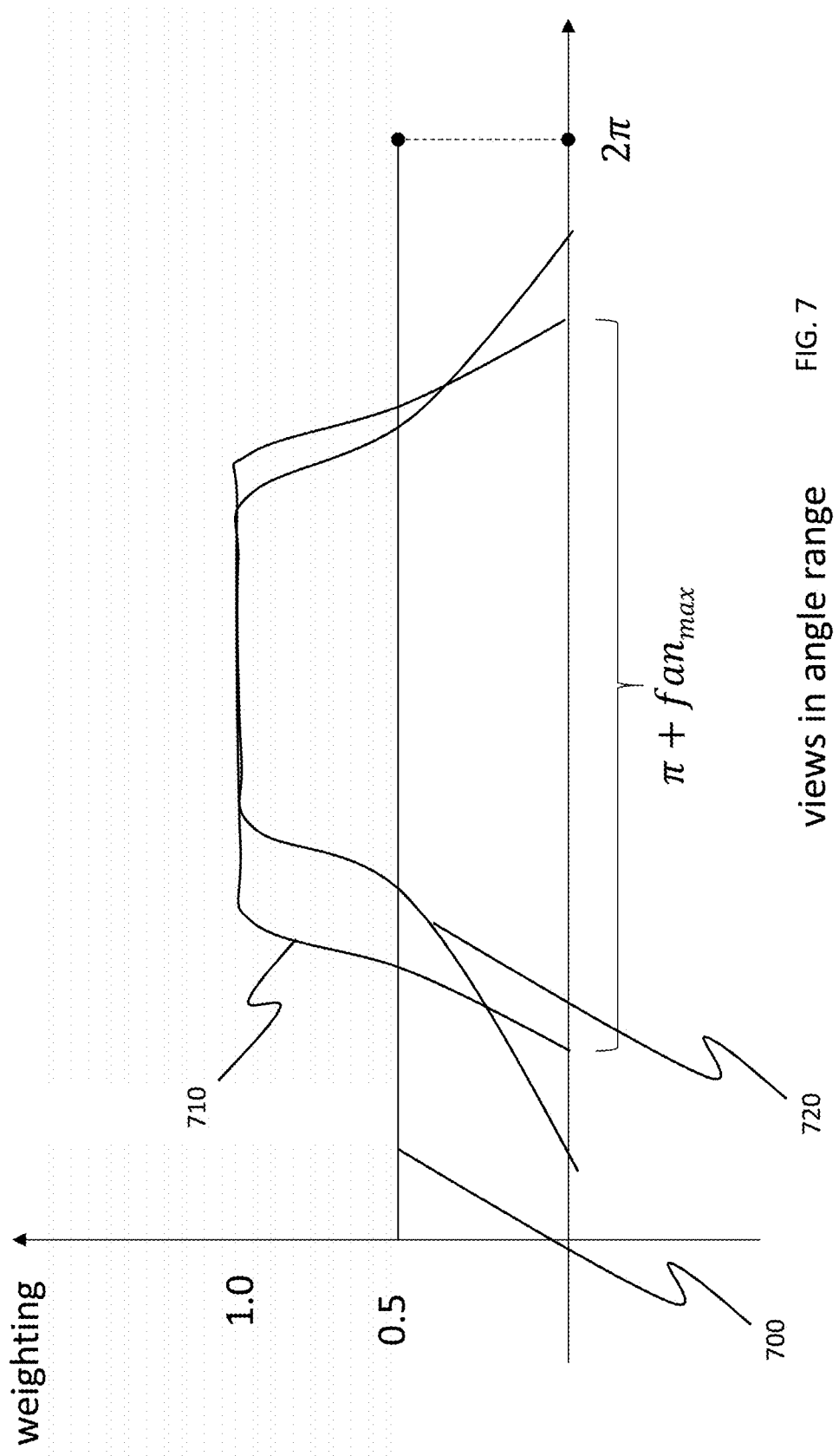
FIG. 7 illustrates a set of three possible weightings for combining complementary rays to produce replacement rays.

In generating replacement views from complementary view, a number of different methods can be applied according to the teachings herein, and the generation of those replacement views can occur at at least two different times. According to a first embodiment, a slice-independent set of replacements can be performed. In such an embodiment, the replacement rays are calculated without regard to in which slice the missing data is to be used. For example, when the data is first acquired, the system detects that a number of consecutive views are missing, and the missing views are replaced with replacement views once, thereby creating an augmented set of views. The augmented set of views can then be processed like error-free sets of views and image reconstructions are performed normally. In such cases, any of the above techniques can be performed. For example, (1) replacing missing rays within each missing view with a corresponding ray from complementary views when only one complementary ray exists in the complementary view per missing ray, and (2) replacing missing rays within each missing view with a weighted combination of corresponding rays from complementary views when plural complementary rays exist per missing ray. The weighted combination may include any one of: (1) an average of a fixed number or fixed percentage of the corresponding complementary rays, (2) an average of all of the corresponding complementary rays, (3) a linear or non-linear combination of a fixed number or fixed percentage of the corresponding complementary rays, and (4) a linear or non-linear combination of corresponding complementary rays within a fixed angular range from the missing view(s). The combinations may include constant weights or weights that decrease based on a distance between the missing ray and the complementary ray being weighted such that complementary rays nearer the missing ray are weighted more heavily in the combination. FIG. 7 shows a graph of three possible weightings that are specific to rays within a view. When an error-free scan would have had the same ray redundancy for all views used in a reconstruction, each complementary ray within a maximum fixed range (centered on the missing ray) are combined in a first combination using a half weight 700 (i.e., by multiplying each ray by 0.5). In a second weighting 710, complementary rays within $\pi+\text{fan}_{max}$ radians are weighted to produce a half-weight, where $\text{fan}_{max}$ is the change between the maximum and minimum fan angle used in the view. In a third weighting 720, a specialized function using "over-half" weighting is used when handling data for more than half a rotation plus $\text{fan}_{max}$ but less than a full rotation.

Figure 8:
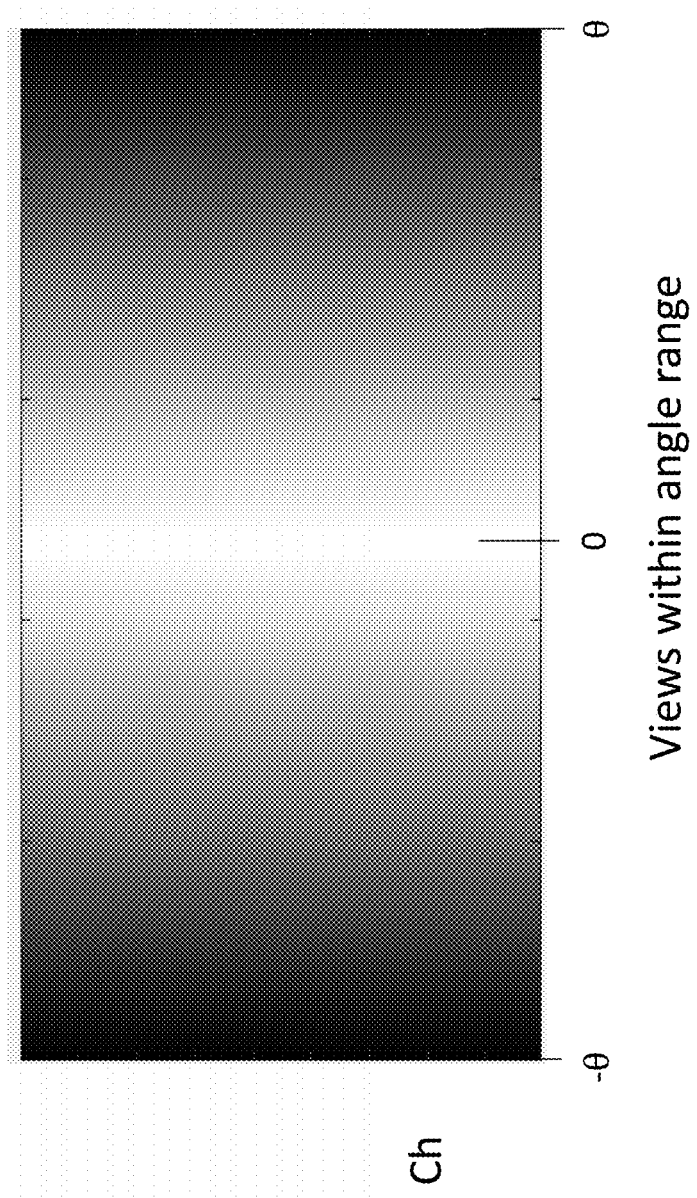
FIG. 8 illustrates a graph of a set of known weights acting as a sliding window of weights used to perform an image reconstruction.

According to a second embodiment, a slice-dependent set of replacements can be performed, as may be used in helical reconstructions. FIG. 8 shows a graph of a set of known weights being used as a sliding window for the rays within a series of views that are being used to reconstruct a slice. The illustrated graph represents how weighting slides between views as a slice to be reconstructed changes. According to helical pitch (circular scan: pitch=0), detector Z coverage, desired noise level and temporal resolution, an available data range (from $-\theta$ to $\theta$) can be selected for each slice to do image reconstruction. FIG. 8 shows one example of the redundancy weights being used over the data range, but the disclosure is not limited to the illustrated mapping of redundancy weights. In locations in the graph with lighter values (i.e., closer to white), a higher weight is used for the rays in the corresponding view. In locations in the graph with darker values (i.e., closer to black), a lower weight is used for the rays in the corresponding view. In the graph, the illustrated weightings include 100% at a center (corresponding to angle 0), and drop to 0% at the edges using a linearly decrease (i.e., have a 50% weighting at the views corresponding to angles $\theta/2$ and $-\theta/2$ and having a 25% weighting at the views corresponding to angles $3\theta/4$ and $-3\theta/4$). Views corresponding to angles greater than $\theta$ and less than $-\theta$ are assigned weights of 0%. In addition, although the weights are illustrated as being channel independent, in an alternate embodiment weights can vary in a channel dependent manner as well.

Figure 9:
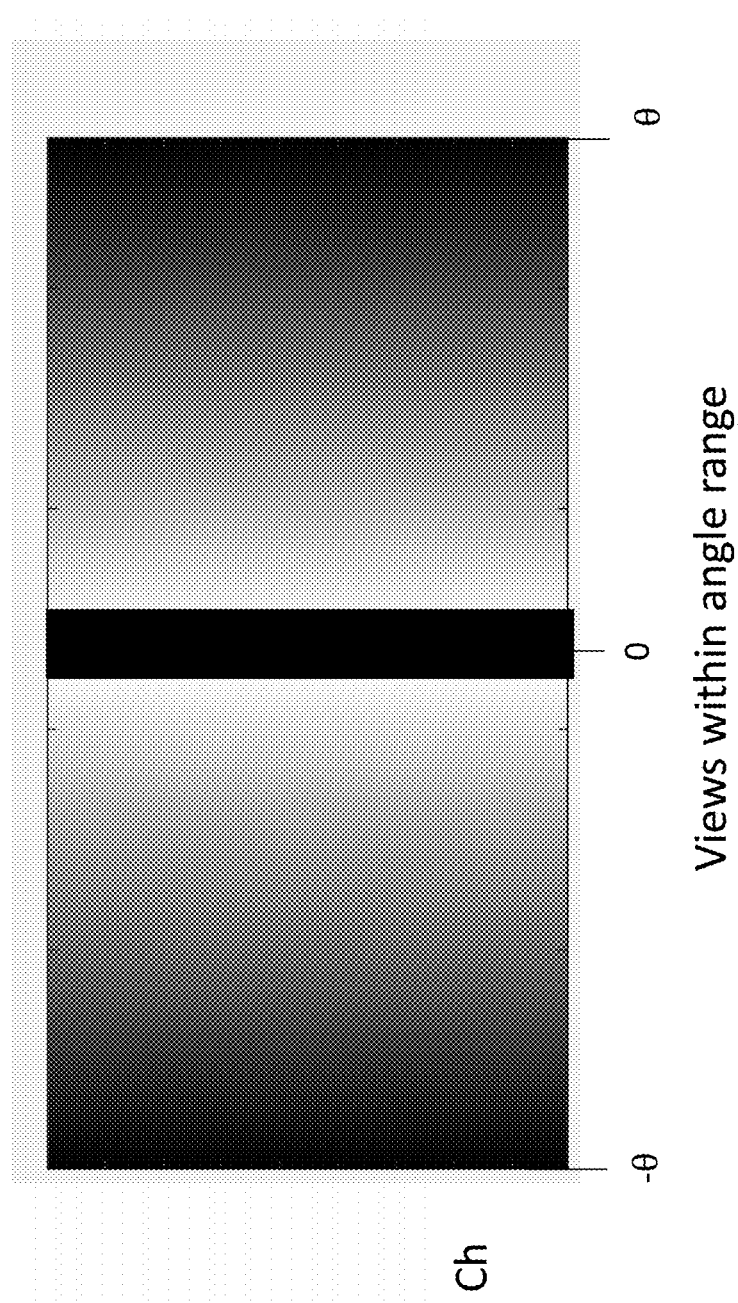
FIG. 9 illustrates the graph of FIG. 8 but in a case where the 100 views in the middle are missing.
Figure 10:
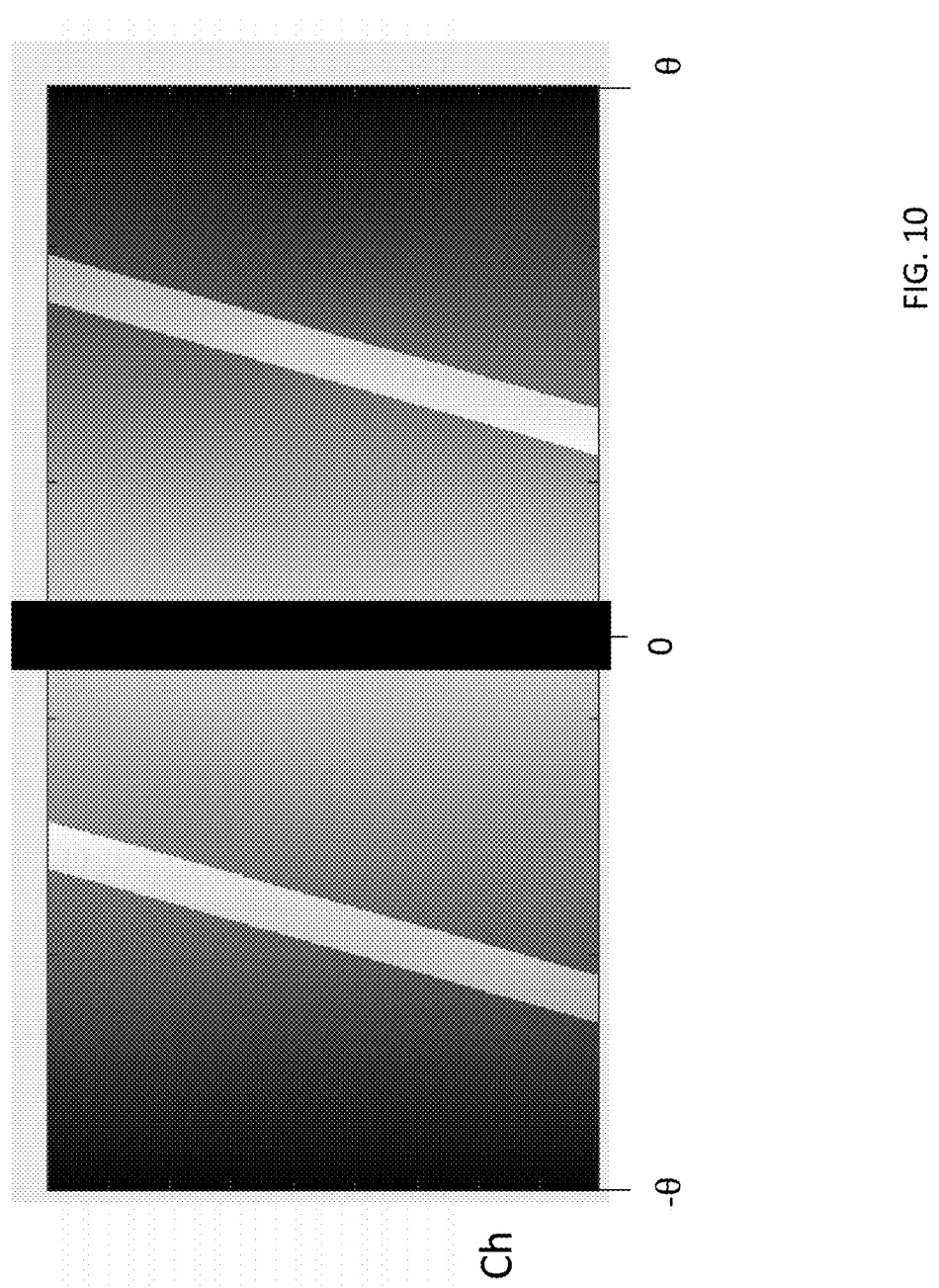
FIG. 10 illustrates a modified version of the graph of FIG. 8 in a case where the weights that should have been applied to the missing views are instead applied to the complementary views.
Figures 11A, 11B:
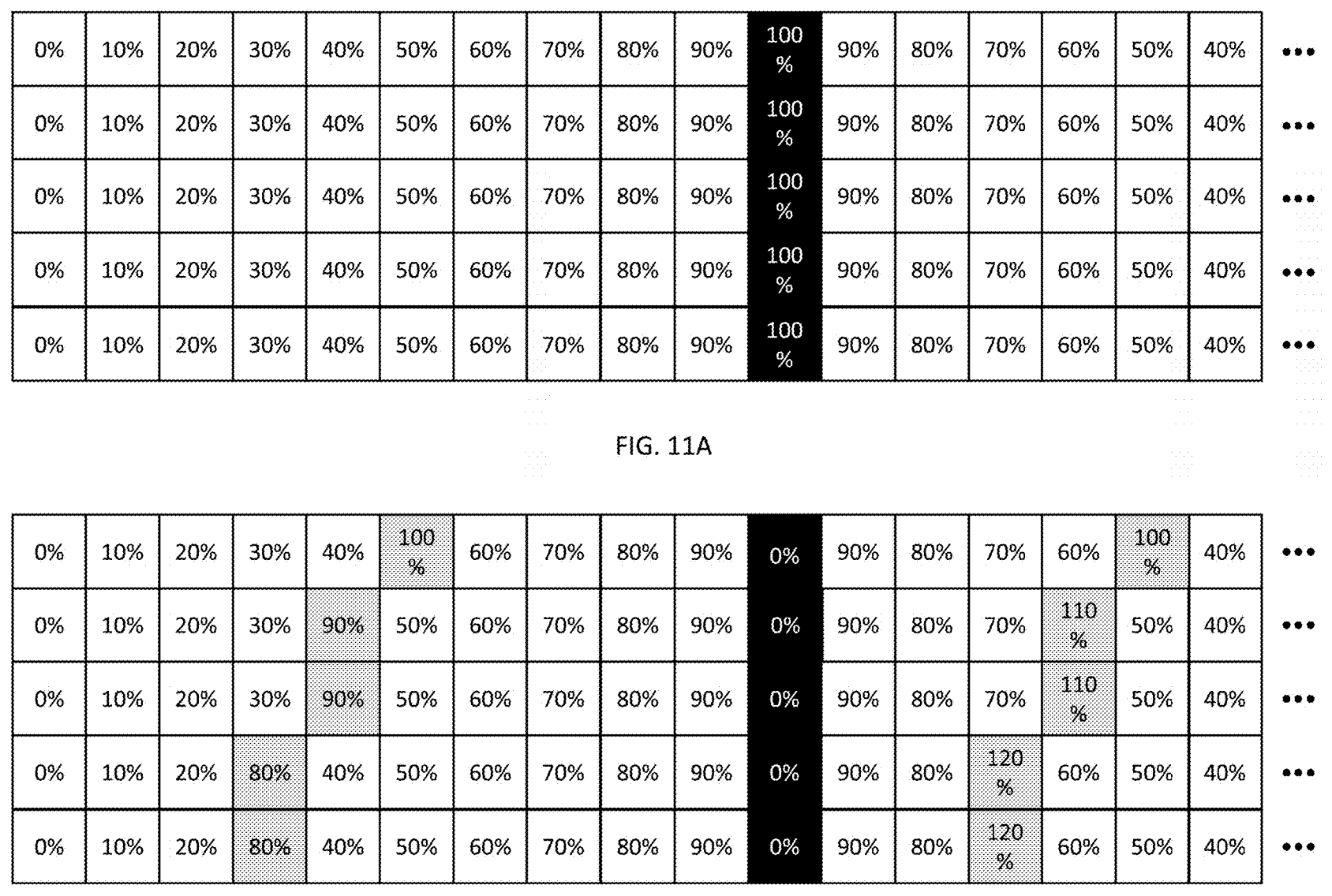

FIG. 9 shows the graph of FIG. 8 but in a case where a large number of consecutive views (e.g., 100 views) in the middle of the sliding window are missing, i.e., corresponding to where the slice is being reconstructed. In the illustrated example, more data is available than within the range $(-\theta, \theta)$, but data outside that range is weighted as 0%. In the illustrated embodiment, each of the missing rays is contained in at least two complementary views. Assuming that the weights that should have been applied to the rays of the missing views are instead applied to the rays of the complementary views, a new set of weighting is produced, as shown in FIG. 10, on a ray-by-ray basis. As can be seen therein, the higher weights that used to be associated with the missing views are instead divided between two diagonal bands (whose slopes depend on the pitch of the helical scan), effectively "filling-in" the missing views by weighting other complementary data views to overcome the zero effect of the missing views. In the illustrated embodiment, because the weights of missing middle views are being divided between two complementary rays, each of the corresponding portions of the diagonal bands is lighter (i.e., is afforded a higher weight) than its original weighting. That is, the middle views now have their weights divided in half and assigned to the complementary views. This change in weights is shown numerically for a smaller number of values in FIGS. 11A-11D. In FIG. 11A, the missing views are illustrated as being in the middle. In such a case, as can be seen in the first row of FIG. 11B, the 100% weighting from the middle views was divided 50%/50% and assigned to each of the 50% boxes to give two top boxes with weights of 100%. In the second row, the 100% weighting from the middle was divided 50%/50% and assigned to each of a 40% box and a 60% box to give two second row boxes with increased weights of 90% and 110%, respectively. By comparison, in FIG. 11C, the missing views are illustrated as being before the middle. In such a case, as can be seen in the first row of FIG. 11D, the 60% weighting from the missing views was divided 50%/50% and assigned to the first 10% box and the second 90% box to give two top boxes with weights of 40% and 120%, respectively. In the second row, the 60% weighting from the missing views was divided 50%/50% and assigned to each of a 0% box and a 100% box to give two second row boxes with increased weights of 30% and 130%, respectively. By comparing FIGS. 11A-11D, the weighted combination of the complementary rays can be seen to be a weighted combination based on an angular position of a missing ray with respect to the image data being reconstructed.

Figures 12A, 12B, 12C:
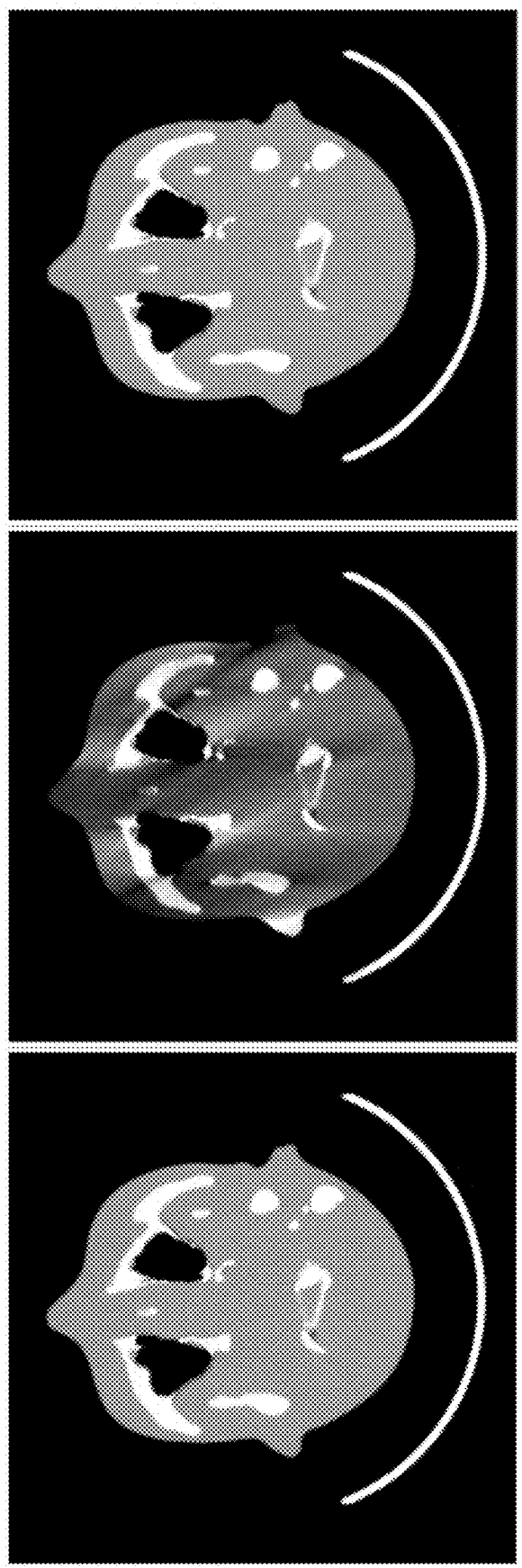
FIGS. 12A-12C are images showing an original reconstructed slice, a reconstructed slice with 50 consecutive missing views in the middle, and a reconstructed slice with 50 consecutive missing views in the middle having been replaced by weighed complementary views, respectively.
Figures 13A, 13B, 13C:
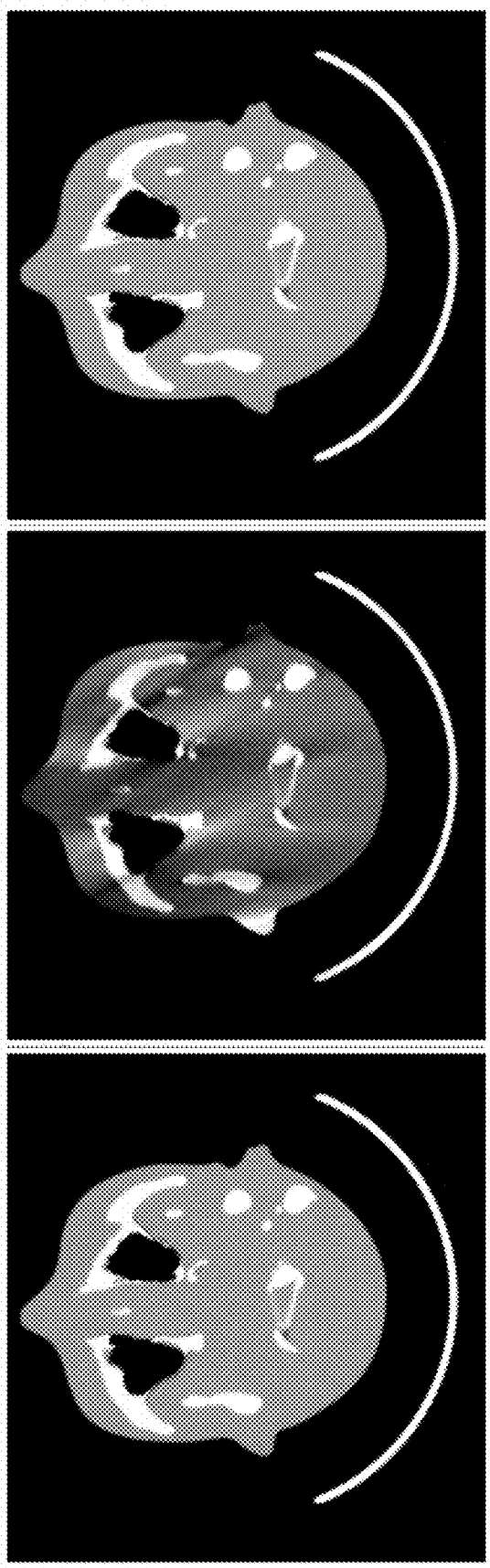
FIGS. 13A-13C are images showing an original reconstructed slice, a reconstructed slice with 100 consecutive missing views in the middle, and a reconstructed slice with 100 consecutive missing views in the middle having been replaced by weighed complementary views, respectively.

FIGS. 12A-12C are images showing an original reconstructed slice, a reconstructed slice with 50 consecutive missing views in the middle, and a reconstructed slice with 50 consecutive missing views in the middle having been replaced by weighed complementary views, respectively. FIGS. 13A-13C are images showing an original reconstructed slice, a reconstructed slice with 100 consecutive missing views in the middle, and a reconstructed slice with 100 consecutive missing views in the middle having been replaced by weighed complementary views, respectively.

Figures 11C, 11D:
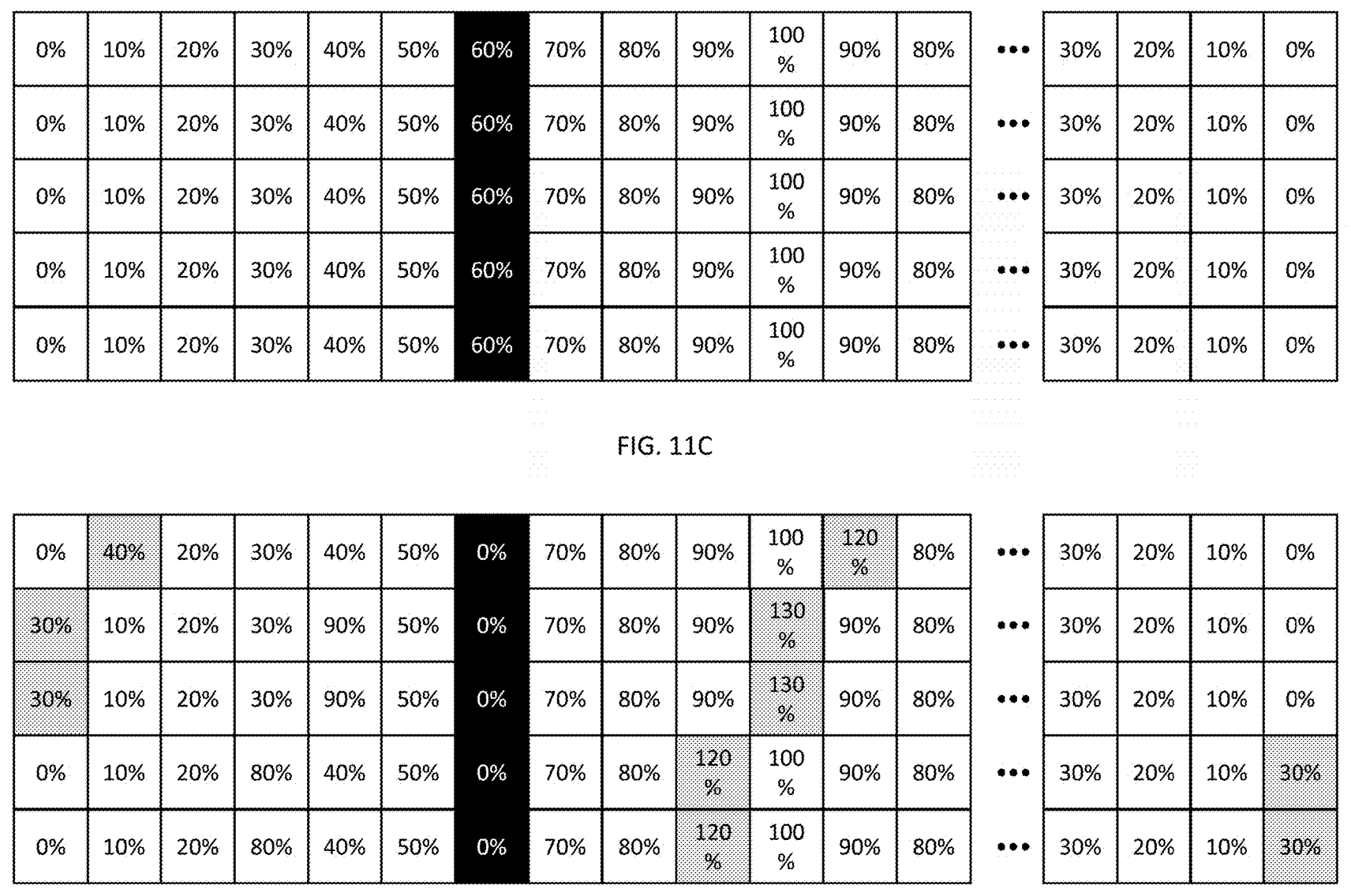
Figure 14:
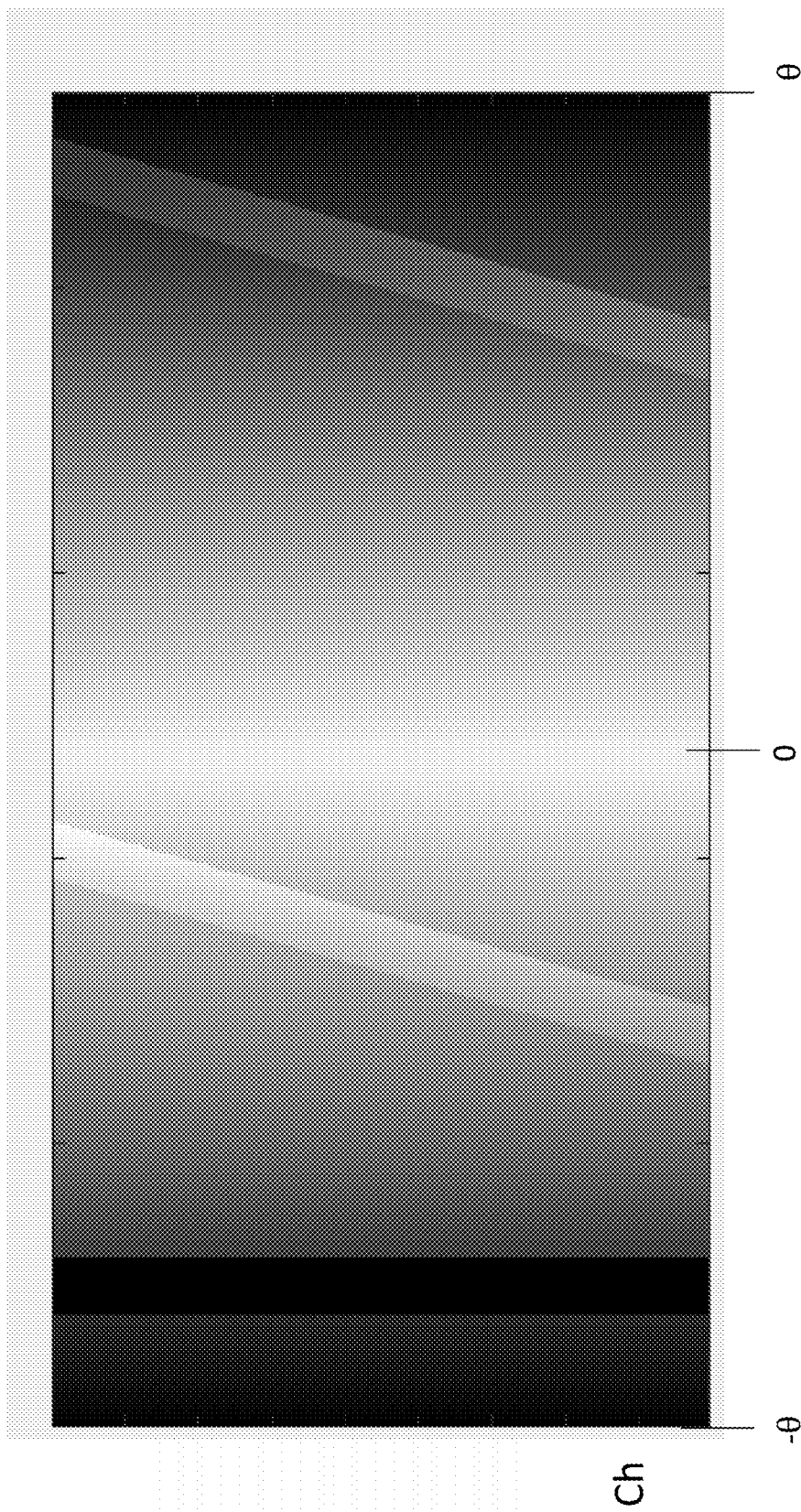
FIG. 14 illustrates a modified version of the graph of FIG. 8 in a case where missing views are centered around a view near angle −7θ/8 and the weights that should have been applied to the missing views are instead applied to the complementary views.
Figures 15A, 15B:
FIGS. 15A and 15B are images showing an original reconstructed slice and a reconstructed slice with the consecutive missing views of FIG. 14 having been replaced by weighed complementary views.

Similar to FIG. 11D, FIG. 14 illustrates a modified version of the graph of FIG. 8 in a case where missing views are centered around a view near angle −7θ/8 and the weights that should have been applied to the missing views are instead applied to the complementary views. FIGS. 15A and 15B are images showing an original reconstructed slice and a reconstructed slice with the consecutive missing views of FIG. 14 having been replaced by weighed complementary views.

Figure 16:
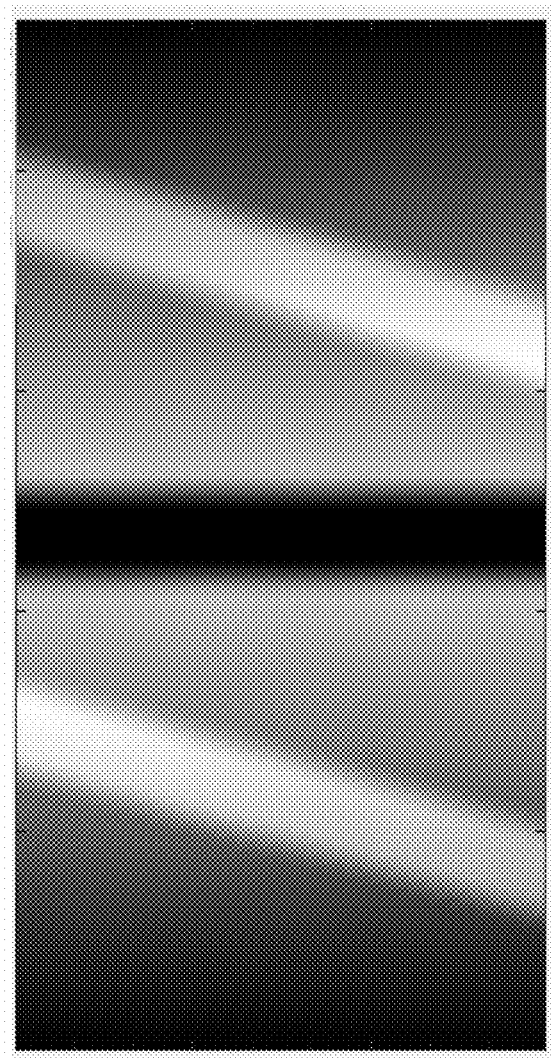
FIG. 16 illustrates a smoothed set of redundancy weights used to smooth the transition between data from missing views and error-free data.

Using weightings such as in FIGS. 10, 11A-11D, and 14 causes abrupt changes adjacent between weightings as compares with the original weightings of FIG. 8. As such, streaks may be introduced into the resulting reconstructed image that may be smoothed out using alternate weightings. FIG. 16 illustrates a smoothed set of redundancy weights used to smooth the transition between data from missing views and error-free data.

Figures 17A, 17B, 17C:
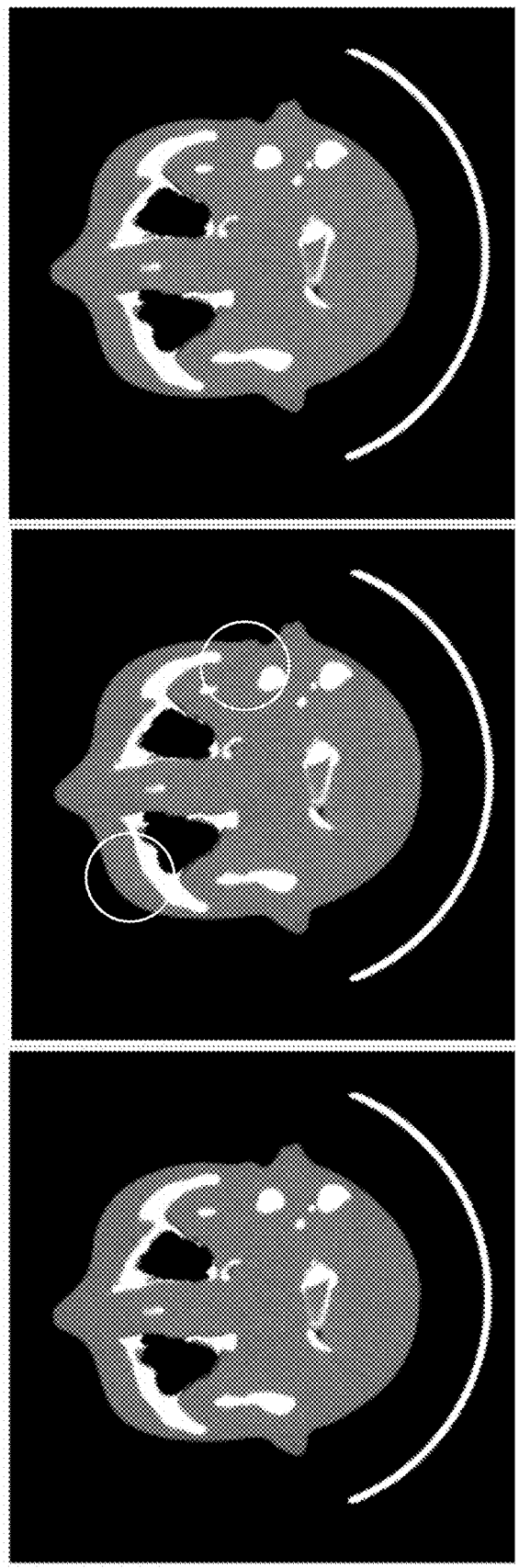
FIGS. 17A-17C illustrate the effects of the smoothing on a reconstructed slice acquired under a first set of scanning conditions.

FIGS. 17A-17C illustrate the effects of the smoothing on a reconstructed slice acquired under a first set of scanning conditions. FIG. 17A is an original reconstructed image without a gap in the views. FIG. 17B is a reconstructed image using a non-smoothed weighting of FIG. 10. As compared with the original, there is a brighter shading in the left circle and a streak in the right circle. Using the smoothed weighting of FIG. 16, the slice of FIG. 17C is reconstructed without the change in shading or the streak, thereby more closely representing the original slice.

Figures 18A, 18B, 18C:
FIGS. 18A-18C illustrate the effects of the smoothing on a reconstructed slice acquired under a second set of scanning conditions for the same slice as in FIGS. 17A-17C.

FIGS. 18A-18C illustrate the effects of the smoothing on a reconstructed slice acquired under a second set of scanning conditions for the same slice as in FIGS. 17A-17C. FIG. 18A is an original reconstructed image without a gap in the views. FIG. 18B is a reconstructed image using a non-smoothed weighting of FIG. 10. As compared with the original, there is a brighter shading in the left circle and a streak in the right circle. Using the smoothed weighting of FIG. 16, the slice of FIG. 18C is reconstructed without the change in shading or the streak, thereby more closely representing the original slice.

Figure 19A:
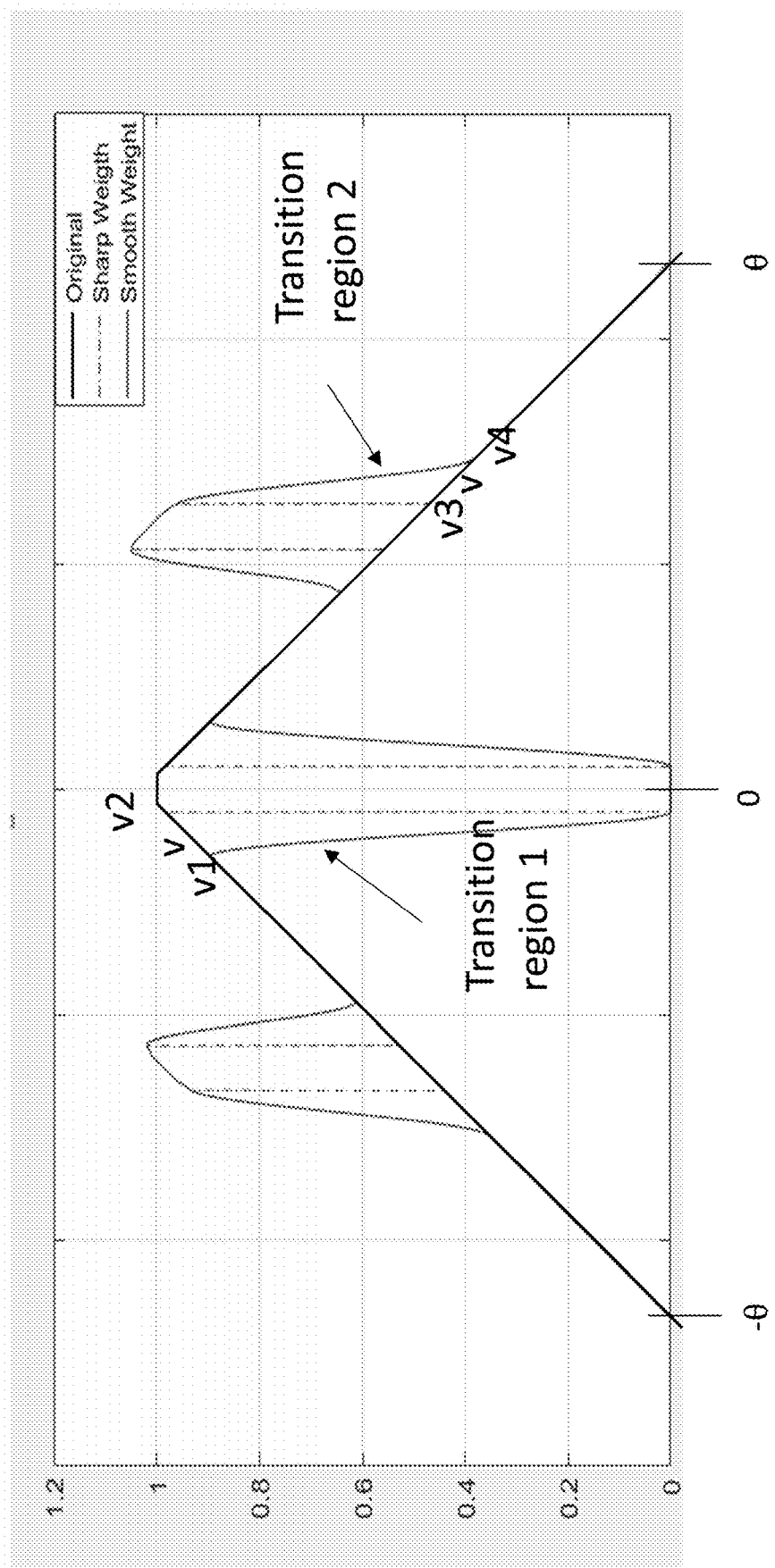
FIGS. 19A and 19B illustrate exemplary weighting functions.
Figure 19B:
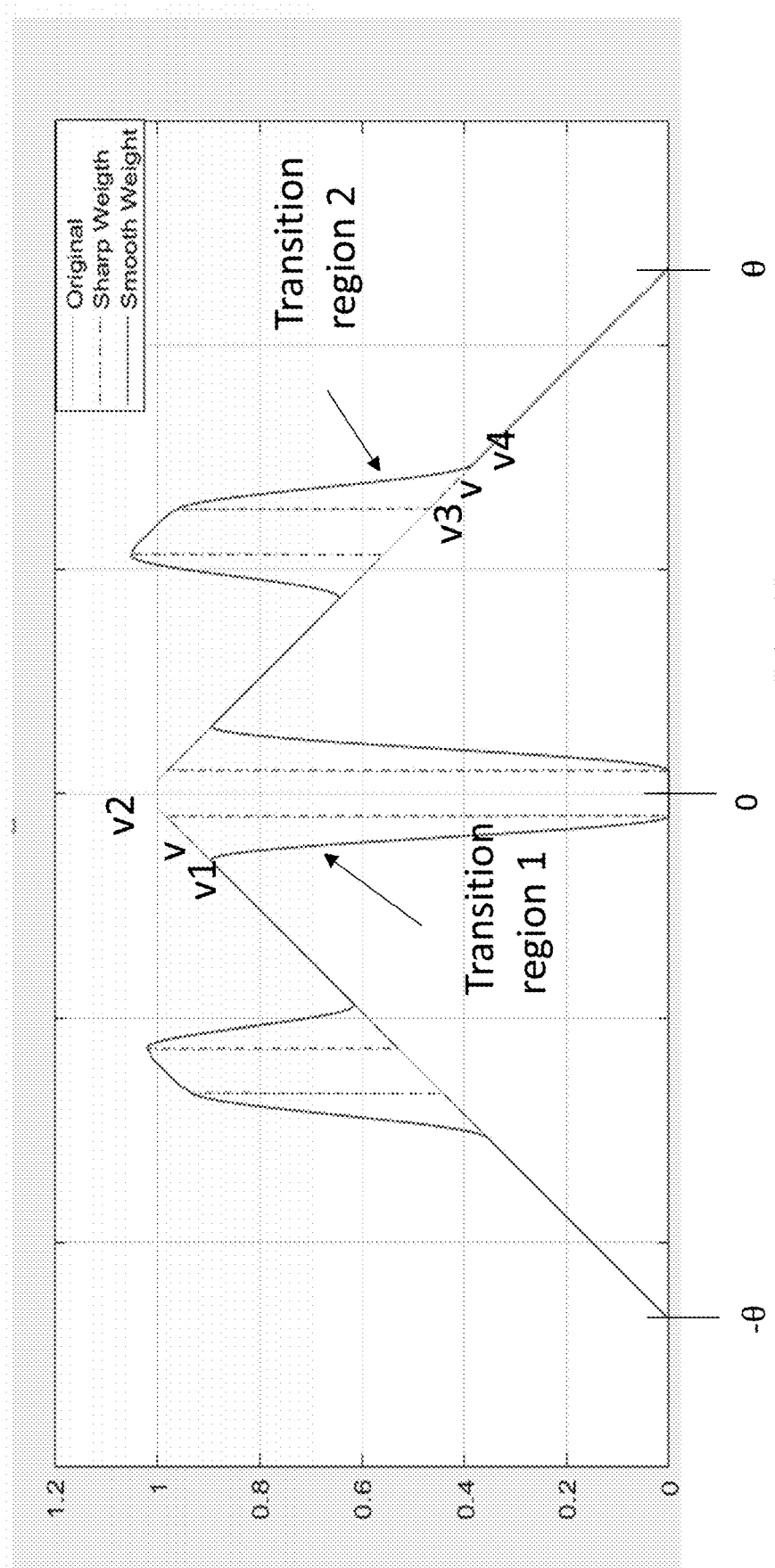
Figures 21A, 21B, 21C:
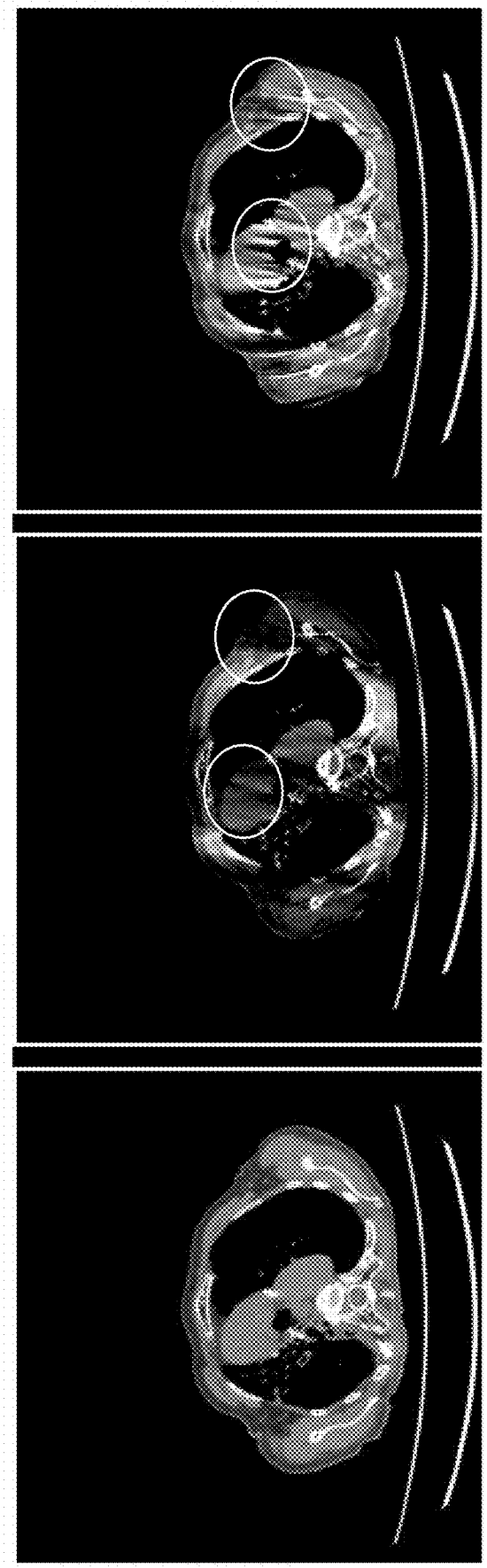
FIG. 21A illustrates an original reconstructed image generated using all of the views obtained during a scan of soft tissue where no views were considered "missing."
FIG. 21B illustrates a test reconstructed image generated using the data of FIG. 21A but by removing a number of consecutive views to simulate "missing" views before the reconstructed image was generated.
FIG. 21C illustrates a test reconstructed image generated using linear interpolation on data of FIG. 21A after first removing a number of consecutive views to simulate "missing" views and which contains streaks as compared to FIG. 21A.
Figures 22A, 22B, 22C:
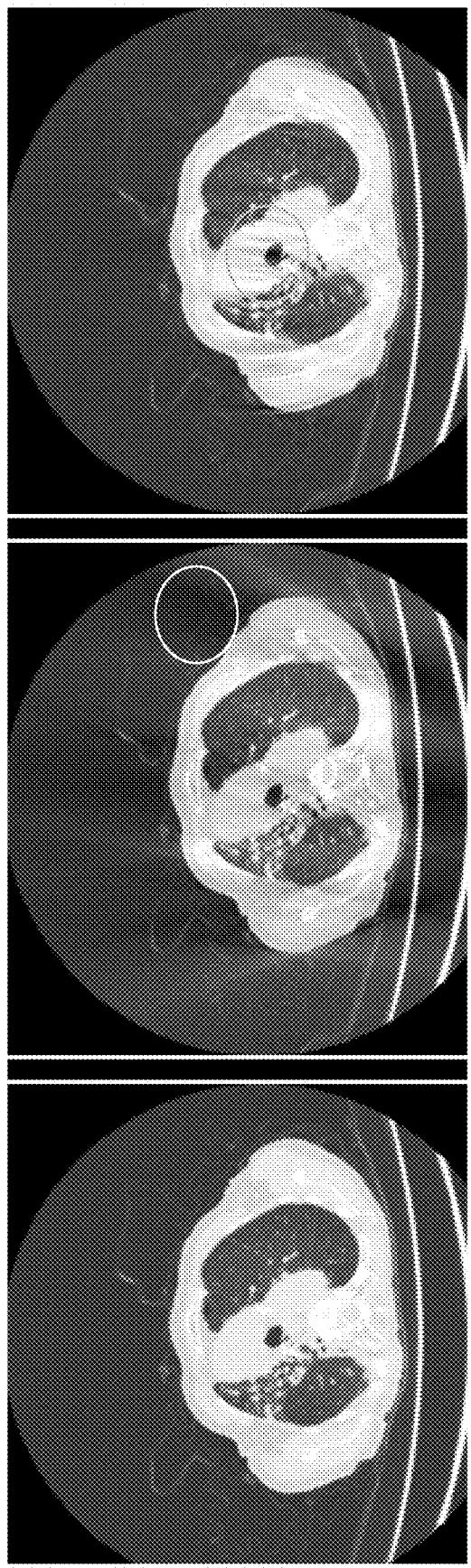
FIG. 22A illustrates an original reconstructed image generated using all of the views obtained during a scan of human lungs where no views were considered "missing."
FIG. 22B illustrates a test reconstructed image generated using the data of FIG. 22A but by removing a number of consecutive views to simulate "missing" views before the reconstructed image was generated, thereby introducing unintended shading.
FIG. 22C illustrates a test reconstructed image generated using linear interpolation on data of FIG. 22A after first removing a number of consecutive views to simulate "missing" views and which contains streaking as compared to FIG. 22A.

FIGS. 19A and 19B illustrate weighting functions as described herein. FIG. 19A shows a series of thick lines forming a pyramid corresponding to the original weightings of FIG. 8. To accentuate the other weightings, the original weighting of FIG. 8 is shown lightly in FIG. 19B which instead accentuates the weighting applied in FIG. 10 as compared to FIG. 16. The smoothed weighting of FIG. 16 is shown as a solid line that transitions slowly compared to the dotted liens corresponding to the non-smoothed weightings of FIG. 10. To produce the smoothed weightings of FIGS. 16, 19A, and 19B, the original weightings (W) of FIG. 10 were used as a starting point. The smoothed weightings (Ws) were then generated according to Ws=W+dW. dW is the smoothing part, and it is non-zero only in transition ranges. To hold the amounts of redundancy constant, the smoothing part and its complementary parts were changed as show in transition regions 1 and 2. The transition range 1 is from view angle v1 to view angle v2, and v denotes the views in between, then $dW(v)=((\cos(v-v1)/(v2-v1)*pi)-1)/2$. Therefore, to maintain redundancy, for region 2, $dW(v)=1-((\cos(v-v3)/(v4-v3)*pi)-1)/2$. Other redundancy-preserving smoothing functions can be used as well.

Embodiments further include the embodiments set forth in the below noted parentheticals:

(1) A medical image processing method including, but not limited to: obtaining scan data including data corresponding to multiple views acquired in a CT scan of an object to be imaged; obtaining an indication of missing views that were not acquired in the CT scan of the object; determining at least one complementary ray for plural rays corresponding to the missing views that were not acquired in the CT scan of the object; filling in the at least one complementary ray for the plural rays corresponding to the missing views that were not acquired in the CT scan of the object; and reconstructing image data of the object based on the obtained scan data and the filled in at least one complementary ray for the plural rays corresponding to the missing views that were not acquired in the CT scan of the object.

(2) The medical image processing method according to (1), wherein filling in the at least one complementary ray for the plural rays corresponding to the missing views that were not acquired in the CT scan of the object includes, but is not limited to, determining, on a ray-by-ray basis, that the scan data includes a single complementary ray for one ray of one of the missing views, and filling in the one ray with the single complementary ray.

(3) The medical image processing method according to either one of (1) and (2), wherein filling in the at least one complementary ray for the plural rays corresponding to the missing views that were not acquired in the CT scan of the object includes, but is not limited to, determining, on a ray-by-ray basis, that the scan data includes plural complementary rays for one ray of one of the missing views, and filling in the one ray with a weighted combination of the plural complementary rays for the one ray.

(4) The medical image processing method according to (3), wherein the weighted combination is a weighted combination based on an angular position of the one ray with respect to the image data being reconstructed.

(5) The medical image processing method according to any one of (1)-(4), wherein filling in the at least one complementary ray for the plural rays corresponding to the missing views that were not acquired in the CT scan of the object includes, but is not limited to, determining, on a ray-by-ray basis, that the scan data includes plural complementary rays for one ray of one of the missing views, and filling in the one ray with an average of the plural complementary rays for the one ray.

(6) The medical image processing method according to any one of (1)-(5), wherein a number of complementary rays in the plural complementary rays is greater than two.

(7) The medical image processing method according to any one of (1)-(6), wherein determining the at least one complementary ray for plural rays corresponding to the missing views that were not acquired in the CT scan of the object includes, but is not limited to, determining the at least one complementary ray based on a fan angle and a tube angle of the plural rays corresponding to the missing views.

(8) A medical image processing apparatus including, but not limited to: processing circuitry configured to: obtain scan data including data corresponding to multiple views acquired in a CT scan of an object to be imaged; obtain an indication of missing views that were not acquired in the CT scan of the object; determine at least one complementary ray for plural rays corresponding to the missing views that were not acquired in the CT scan of the object; fill in the at least one complementary ray for the plural rays corresponding to the missing views that were not acquired in the CT scan of the object; and reconstruct image data of the object based on the obtained scan data and the filled in at least one complementary ray for the plural rays corresponding to the missing views that were not acquired in the CT scan of the object.

(9) The medical image processing apparatus according to (8), wherein the processing circuitry configured to fill in the at least one complementary ray for the plural rays corresponding to the missing views that were not acquired in the CT scan of the object includes, but is not limited to, processing circuitry configured to determine, on a ray-byray basis, that the scan data includes a single complementary ray for one ray of one of the missing views, and fill in the one ray with the single complementary ray.

(10) The medical image processing apparatus according to either one of (8) and (9), wherein the processing circuitry configured to fill in the at least one complementary ray for the plural rays corresponding to the missing views that were not acquired in the CT scan of the object includes, but is not limited to, processing circuitry configured to determine, on a ray-by-ray basis, that the scan data includes plural complementary rays for one ray of one of the missing views, and fill in the one ray with a weighted combination of the plural complementary rays for the one ray.

(11) The medical image processing apparatus according to (10), wherein the weighted combination is a weighted combination based on an angular position of the one ray with respect to the image data being reconstructed.

(12) The medical image processing apparatus according to any one of (8)-(11), wherein the processing circuitry configured to fill in the at least one complementary ray for the plural rays corresponding to the missing views that were not acquired in the CT scan of the object includes, but is not limited to, processing circuitry configured to determine, on a ray-by-ray basis, that the scan data includes plural complementary rays for one ray of one of the missing views, and fill in the one ray with an average of the plural complementary rays for the one ray.

(13) The medical image processing apparatus according to any one of (8)-(12), wherein a number of complementary rays in the plural complementary rays is greater than two.

(14) The medical image processing apparatus according to any one of (8)-(13), wherein the processing circuitry configured to determine the at least one complementary ray for plural rays corresponding to the missing views that were not acquired in the CT scan of the object includes, but is not limited to, processing circuitry configured to determine the at least one complementary ray based on a fan angle and a tube angle of the plural rays corresponding to the missing views.

(15) A computer storage device including, but not limited to: a non-transitory computer-readable medium including instructions stored therein which, when read and executed by a computer processor, cause the computer processor to perform the steps of: obtaining scan data including data corresponding to multiple views acquired in a CT scan of an object to be imaged; obtaining an indication of missing views that were not acquired in the CT scan of the object; determining at least one complementary ray for plural rays corresponding to the missing views that were not acquired in the CT scan of the object; filling in the at least one complementary ray for the plural rays corresponding to the missing views that were not acquired in the CT scan of the object; and reconstructing image data of the object based on the obtained scan data and the filled in at least one complementary ray for the plural rays corresponding to the missing views that were not acquired in the CT scan of the object.

(16) A computer storage device according to (15), wherein the computer instructions stored in the non-transitory computer-readable medium, when read and executed by the computer processor, cause the computer processor to perform the methods according to any one of (2)-(7).

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Moreover, any of the elements of the appended claims may be used in conjunction with any other claim element. Rather, any limitations to embodiments of the invention are presented in the following claims.

What is claimed is:

1. A medical image processing method, comprising:
    obtaining scan data including data corresponding to multiple views acquired in a CT scan of an object to be imaged;
    identifying plural rays in the scan data corresponding to missing views that were not acquired in the CT scan of the object;
    determining at least one complementary ray for the plural rays corresponding to the missing views that were not acquired in the CT scan of the object; and
    reconstructing image data of the object based on the obtained scan data and the determined at least one complementary ray for the plural rays corresponding to the missing views that were not acquired in the CT scan of the object.

2. The medical image processing method of claim 1, further comprising filling in the at least one complementary ray for the plural rays corresponding to the missing views,
    wherein the filling in the at least one complementary ray for the plural rays corresponding to the missing views that were not acquired in the CT scan of the object further comprises determining, on a ray-by-ray basis, that the scan data includes a single complementary ray for one ray of one of the missing views, and filling in the one ray with the single complementary ray.

3. The medical image processing method of claim 1, further comprising filling in the at least one complementary ray for the plural rays corresponding to the missing views,
    wherein the filling in the at least one complementary ray for the plural rays corresponding to the missing views that were not acquired in the CT scan of the object further comprises determining, on a ray-by-ray basis, that the scan data includes plural complementary rays for one ray of one of the missing views, and filling in the one ray with a weighted combination of the plural complementary rays for the one ray.

4. The medical image processing method of claim 3, wherein the weighted combination is a weighted combination based on an angular position of the one ray with respect to the image data being reconstructed.

5. The medical image processing method of claim 1, further comprising filling in the at least one complementary ray for the plural rays corresponding to the missing views,
    wherein the filling in the at least one complementary ray for the plural rays corresponding to the missing views that were not acquired in the CT scan of the object further comprises determining, on a ray-by-ray basis, that the scan data includes plural complementary rays for one ray of one of the missing views, and filling in the one ray with an average of the plural complementary rays for the one ray.

6. The medical image processing method of claim 1, wherein a number of complementary rays in the plural complementary rays is greater than two.

7. The medical image processing method of claim 1, wherein determining the at least one complementary ray for plural rays corresponding to the missing views that were not acquired in the CT scan of the object comprises determining the at least one complementary ray based on a fan angle and a tube angle of the plural rays corresponding to the missing views.

8. A medical image processing apparatus, comprising:
processing circuitry configured to
obtain scan data including data corresponding to multiple views acquired in a CT scan of an object to be imaged;
identify plural rays in the scan data corresponding to missing views that were not acquired in the CT scan of the object;
determine at least one complementary ray for the plural rays corresponding to the missing views that were not acquired in the CT scan of the object; and
reconstruct image data of the object based on the obtained scan data and the determined at least one complementary ray for the plural rays corresponding to the missing views that were not acquired in the CT scan of the object.

9. The medical image processing apparatus of claim 8, wherein the processing circuitry is further configured to
fill in the at least one complementary ray for the plural rays corresponding to the missing views by determining, on a ray-by-ray basis, that the scan data includes a single complementary ray for one ray of one of the missing views, and fill in the one ray with the single complementary ray.

10. The medical image processing apparatus of claim 8, wherein the processing circuitry is further configured to
fill in the at least one complementary ray for the plural rays corresponding to the missing views by determining, on a ray-by-ray basis, that the scan data includes plural complementary rays for one ray of one of the missing views, and fill in the one ray with a weighted combination of the plural complementary rays for the one ray.

11. The medical image processing apparatus of claim 10, wherein the weighted combination is a weighted combination based on an angular position of the one ray with respect to the image data being reconstructed.

12. The medical image processing apparatus of claim 8, wherein the processing circuitry is further configured to fill in the at least one complementary ray for the plural rays corresponding to the missing views by determining, on a ray-by-ray basis, that the scan data includes plural complementary rays for one ray of one of the missing views, and fill in the one ray with an average of the plural complementary rays for the one ray.

13. The medical image processing apparatus of claim 8, wherein a number of complementary rays in the plural complementary rays is greater than two.

14. The medical image processing apparatus of claim 8, wherein the processing circuitry is further configured to determine the at least one complementary ray for plural rays corresponding to the missing views that were not acquired in the CT scan of the object by determining the at least one complementary ray based on a fan angle and a tube angle of the plural rays corresponding to the missing views.

15. A computer storage device, comprising:
a non-transitory computer-readable medium including instructions stored therein which, when read and executed by a computer processor, cause the computer processor to perform the steps of:
obtaining scan data including data corresponding to multiple views acquired in a CT scan of an object to be imaged;
identifying plural rays in the scan data corresponding to missing views that were not acquired in the CT scan of the object;
determining at least one complementary ray for plural rays corresponding to missing views that were not acquired in the CT scan of the object; and
reconstructing image data of the object based on the obtained scan data and the determined at least one complementary ray for the plural rays corresponding to the missing views that were not acquired in the CT scan of the object.

16. The medical image processing method of claim 1, further comprising setting weight data for the determined at least one complementary ray based on a position of missing views in the scan data.

17. The medical image processing method of claim 16, further comprising performing a smoothing process on the scan data containing the determined at least one complementary ray to which weight data is set.

18. The medical image processing apparatus of claim 8, wherein the processing circuitry is further configured to set weight data for the determined at least one complementary ray based on a position of missing views in the scan data.

19. The medical image processing method of claim 18, wherein the processing circuitry is further configured to perform a smoothing process on the scan data containing the determined at least one complementary ray to which weight data is set.

20. The medical image processing method of claim 1, further comprising identifying a ray that is part of a view having corresponding data determined to be unreliable or unusable.

* * * * *